US012741093B2

(12) United States Patent
Nazzaro et al.

(10) Patent No.: US 12,741,093 B2

(45) Date of Patent: Sep. 22, 2026

(54) ADAPTATION OF A MEDICAMENT DELIVERY DEVICE TO CHANGING ENVIRONMENTAL CONDITIONS

(71) Applicant: Insulet Corporation, Acton, MA (US)

(72) Inventors: David Nazzaro, Groveland, MA (US); Rangarajan Narayanaswami, Weston, MA (US)

(73) Assignee: INSULET CORPORATION, Acton, MA (US)

( * ) Notice: Subject to any disclaimer, the term of this patent is extended or adjusted under 35 U.S.C. 154(b) by 666 days.

(21) Appl. No.: 18/306,061

(22) Filed: Apr. 24, 2023

(65) Prior Publication Data

US 2023/0347053 A1 Nov. 2, 2023

Related U.S. Application Data

(60) Provisional application No. 63/335,493, filed on Apr. 27, 2022.

(51) Int. Cl.

*A61M 5/172* (2006.01)
*A61M 5/142* (2006.01)
*A61M 5/168* (2006.01)

(52) U.S. Cl.

CPC .......... *A61M 5/1723* (2013.01); *A61M 5/142* (2013.01); *A61M 5/16831* (2013.01); (Continued)

(58) Field of Classification Search

CPC ........... A61M 2005/14264; A61M 5/142–155; A61M 5/16831; H04M 2250/10; H04M 2250/12; H04W 4/027; H04W 4/029

See application file for complete search history.

(56) References Cited

U.S. PATENT DOCUMENTS 303,013 A 8/1884 Horton
445,545 A 2/1891 Crane
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Stephanie Sebasco Cheng

(74) *Attorney, Agent, or Firm* — Goodwin Procter LLP

(57) ABSTRACT

The exemplary embodiments may detect the changed ambient air pressure and may adjust settings for the medicament delivery device to compensate for the changed ambient air pressure. The exemplary embodiments may detect the changed ambient air pressure and may adjust settings for the medicament delivery device to compensate for the changed ambient air pressure. Based on the detection of these events, the medicament delivery device may be switched into a flight mode. In the flight mode, medicament boluses may be reduced to nominal dosages, basal delivery rates may be modified and sample periods for sensors, like glucose monitors, may be shortened to sample sensor values more frequently. The exemplary embodiments may prohibit delivery of medicament during times of changing ambient air pressure to avoid over-delivering or under-delivering the medicament due to the ambient air pressure level.

20 Claims, 26 Drawing Sheets

(52) U.S. Cl.
CPC ............ *A61M 2005/14208* (2013.01); *A61M 2005/14264* (2013.01); *A61M 2202/0486* (2013.01)

(56) References Cited

U.S. PATENT DOCUMENTS 588,583 A 8/1897 Lade
1,441,508 A 1/1923 Marius
2,283,925 A 5/1942 Harvey
2,797,149 A 6/1957 Skeggs
2,886,529 A 5/1959 Guillaud
3,574,114 A 4/1971 Monforte
3,614,554 A 10/1971 Shield
3,631,847 A 1/1972 Hobbs
3,634,039 A 1/1972 Brondy
3,812,843 A 5/1974 Wootten et al.
3,841,328 A 10/1974 Jensen
3,885,662 A 5/1975 Schaefer
3,963,380 A 6/1976 Thomas, Jr. et al.
3,983,077 A 9/1976 Fuller et al.
4,055,175 A 10/1977 Clemens et al.
4,108,177 A 8/1978 Pistor
4,146,029 A 3/1979 Ellinwood, Jr.
4,151,845 A 5/1979 Clemens
4,245,634 A 1/1981 Albisser et al.
4,268,150 A 5/1981 Chen
4,313,439 A 2/1982 Babb et al.
4,368,980 A 1/1983 Aldred et al.
4,373,527 A 2/1983 Fischell
4,400,683 A 8/1983 Eda et al.
4,403,984 A 9/1983 Ash et al.
4,424,720 A 1/1984 Bucchianeri
4,435,173 A 3/1984 Siposs et al.
4,464,170 A 8/1984 Clemens et al.
4,469,481 A 9/1984 Kobayashi
4,475,901 A 10/1984 Kraegen et al.
4,498,843 A 2/1985 Schneider et al.
4,507,115 A 3/1985 Kambara et al.
4,523,170 A 6/1985 Huth, III
4,526,568 A 7/1985 Clemens et al.
4,526,569 A 7/1985 Bernardi
4,529,401 A 7/1985 Leslie et al.
4,551,134 A 11/1985 Slavik et al.
4,559,033 A 12/1985 Stephen et al.
4,559,037 A 12/1985 Franetzki et al.
4,562,751 A 1/1986 Nason et al.
4,573,968 A 3/1986 Parker
4,585,439 A 4/1986 Michel
4,601,707 A 7/1986 Albisser et al.
4,624,661 A 11/1986 Arimond
4,633,878 A 1/1987 Bombardieri
4,634,427 A 1/1987 Hannula et al.
4,646,038 A 2/1987 Wanat
4,657,529 A 4/1987 Prince et al.
4,678,408 A 7/1987 Nason et al.
4,684,368 A 8/1987 Kenyon
4,685,903 A 8/1987 Cable et al.
4,731,726 A 3/1988 Allen, III
4,743,243 A 5/1988 Vaillancourt
4,755,169 A 7/1988 Sarnoff et al.
4,755,173 A 7/1988 Konopka et al.
4,759,120 A 7/1988 Bernstein
4,781,688 A 11/1988 Thoma et al.
4,781,693 A 11/1988 Martinez et al.
4,808,161 A 2/1989 Kamen
4,854,170 A 8/1989 Brimhall et al.
4,859,492 A 8/1989 Rogers, Jr. et al.
4,880,770 A 11/1989 Mir et al.
4,886,499 A 12/1989 Cirelli et al.
4,898,578 A 2/1990 Rubalcaba, Jr.
4,898,579 A 2/1990 Groshong et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,944,659 A 7/1990 Labbe et al.
4,967,201 A 10/1990 Rich, III
4,969,874 A 11/1990 Michel et al.
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,007,458 A 4/1991 Marcus et al.
5,062,841 A 11/1991 Siegel
5,084,749 A 1/1992 Losee et al.
5,097,834 A 3/1992 Skrabal
5,102,406 A 4/1992 Arnold
5,109,850 A 5/1992 Blanco et al.
5,125,415 A 6/1992 Bell
5,130,675 A 7/1992 Sugawara
5,134,079 A 7/1992 Cusack et al.
5,139,999 A 8/1992 Gordon et al.
5,153,827 A 10/1992 Coutre et al.
5,154,973 A 10/1992 Imagawa et al.
5,165,406 A 11/1992 Wong
5,176,662 A 1/1993 Bartholomew et al.
5,178,609 A 1/1993 Ishikawa
5,189,609 A 2/1993 Tivig et al.
5,198,824 A 3/1993 Poradish
5,205,819 A 4/1993 Ross et al.
5,207,642 A 5/1993 Orkin et al.
5,213,483 A 5/1993 Flaherty et al.
5,217,754 A 6/1993 Santiago-Aviles et al.
5,219,377 A 6/1993 Poradish
5,232,439 A 8/1993 Campbell et al.
5,237,993 A 8/1993 Skrabal
5,244,463 A 9/1993 Cordner, Jr. et al.
5,254,096 A 10/1993 Rondelet et al.
5,257,980 A 11/1993 Van Antwerp et al.
5,261,882 A 11/1993 Sealfon
5,263,198 A 11/1993 Geddes et al.
5,272,485 A 12/1993 Mason et al.
5,273,517 A 12/1993 Barone et al.
5,281,202 A 1/1994 Weber et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,346,476 A 9/1994 Elson
5,364,342 A 11/1994 Beuchat et al.
5,377,674 A 1/1995 Kuestner
5,380,665 A 1/1995 Cusack et al.
5,385,539 A 1/1995 Maynard
5,389,078 A 2/1995 Zalesky
5,403,797 A 4/1995 Ohtani et al.
5,411,889 A 5/1995 Hoots et al.
5,421,812 A 6/1995 Langley et al.
5,427,988 A 6/1995 Sengupta et al.
5,433,710 A 7/1995 VanAntwerp et al.
5,456,945 A 10/1995 McMillan et al.
5,468,727 A 11/1995 Phillips et al.
5,478,610 A 12/1995 Desu et al.
5,505,709 A 4/1996 Funderburk et al.
5,505,828 A 4/1996 Wong et al.
5,507,288 A 4/1996 Bocker et al.
5,513,382 A 4/1996 Agahi-Kesheh et al.
5,533,389 A 7/1996 Kamen et al.
5,535,445 A 7/1996 Gunton
5,540,772 A 7/1996 McMillan et al.
5,543,773 A 8/1996 Evans et al.
5,558,640 A 9/1996 Pfeiler et al.
5,569,186 A 10/1996 Lord et al.
5,582,593 A 12/1996 Hultman
5,584,053 A 12/1996 Kommrusch et al.
5,584,813 A 12/1996 Livingston et al.
5,590,387 A 12/1996 Schmidt et al.
5,609,572 A 3/1997 Lang
5,614,252 A 3/1997 McMillan et al.
5,625,365 A 4/1997 Tom et al.
5,635,433 A 6/1997 Sengupta
5,637,095 A 6/1997 Nason et al.
5,665,065 A 9/1997 Colman et al.
5,665,070 A 9/1997 McPhee

(56) References Cited

U.S. PATENT DOCUMENTS 5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,707,459 A 1/1998 Itoyama et al.
5,707,715 A 1/1998 deRochemont et al.
5,713,875 A 2/1998 Tanner, II
5,714,123 A 2/1998 Sohrab
5,716,343 A 2/1998 Kriesel et al.
5,722,397 A 3/1998 Eppstein
5,741,228 A 4/1998 Lambrecht et al.
5,746,217 A 5/1998 Erickson et al.
5,747,350 A 5/1998 Sattler
5,747,870 A 5/1998 Pedder
5,748,827 A 5/1998 Holl et al.
5,755,682 A 5/1998 Knudson et al.
5,758,643 A 6/1998 Wong et al.
5,759,923 A 6/1998 McMillan et al.
5,764,189 A 6/1998 Lohninger
5,771,567 A 6/1998 Pierce et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,800,405 A 9/1998 McPhee
5,800,420 A 9/1998 Gross et al.
5,801,057 A 9/1998 Smart et al.
5,804,048 A 9/1998 Wong et al.
5,807,075 A 9/1998 Jacobsen et al.
5,817,007 A 10/1998 Fodgaard et al.
5,820,622 A 10/1998 Gross et al.
5,823,951 A 10/1998 Messerschmidt
5,839,467 A 11/1998 Saaski et al.
5,840,020 A 11/1998 Heinonen et al.
5,848,991 A 12/1998 Gross et al.
5,851,197 A 12/1998 Marano et al.
5,854,608 A 12/1998 Leisten
5,858,005 A 1/1999 Kriesel
5,858,239 A 1/1999 Kenley et al.
5,859,621 A 1/1999 Leisten
5,865,806 A 2/1999 Howell
5,871,470 A 2/1999 McWha
5,879,310 A 3/1999 Sopp et al.
5,889,459 A 3/1999 Hattori et al.
5,891,097 A 4/1999 Saito et al.
5,892,489 A 4/1999 Kanba et al.
5,897,530 A 4/1999 Jackson
5,902,253 A 5/1999 Pfeiffer et al.
5,903,421 A 5/1999 Furutani et al.
5,906,597 A 5/1999 McPhee
5,911,716 A 6/1999 Rake et al.
5,919,167 A 7/1999 Mulhauser et al.
5,931,814 A 8/1999 Alex et al.
5,932,175 A 8/1999 Knute et al.
5,933,121 A 8/1999 Rainhart et al.
5,935,099 A 8/1999 Peterson et al.
5,945,963 A 8/1999 Leisten
5,947,911 A 9/1999 Wong et al.
5,957,890 A 9/1999 Mann et al.
5,961,492 A 10/1999 Kriesel et al.
5,965,848 A 10/1999 Altschul et al.
5,971,941 A 10/1999 Simons et al.
5,993,423 A 11/1999 Choi
5,997,501 A 12/1999 Gross et al.
6,017,318 A 1/2000 Gauthier et al.
6,019,747 A 2/2000 McPhee
6,023,251 A 2/2000 Koo et al.
6,024,539 A 2/2000 Blomquist
6,027,826 A 2/2000 deRochemont et al.
6,028,568 A 2/2000 Asakura et al.
6,031,445 A 2/2000 Marty et al.
6,032,059 A 2/2000 Henning et al.
6,036,924 A 3/2000 Simons et al.
6,040,578 A 3/2000 Malin et al.
6,040,805 A 3/2000 Huynh et al.
6,046,707 A 4/2000 Gaughan et al.
6,049,727 A 4/2000 Crothall
6,050,978 A 4/2000 Orr et al.
6,052,040 A 4/2000 Hino
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.
6,111,544 A 8/2000 Dakeya et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,143,432 A 11/2000 de Rochemont et al.
6,154,176 A 11/2000 Fathy et al.
6,157,041 A 12/2000 Thomas et al.
6,161,028 A 12/2000 Braig et al.
6,162,639 A 12/2000 Douglas
6,174,300 B1 1/2001 Kriesel et al.
6,176,004 B1 1/2001 Rainhart et al.
6,181,297 B1 1/2001 Leisten
6,188,368 B1 2/2001 Koriyama et al.
6,190,359 B1 2/2001 Heruth
6,195,049 B1 2/2001 Kim et al.
6,196,046 B1 3/2001 Braig et al.
6,200,287 B1 3/2001 Keller et al.
6,200,293 B1 3/2001 Kriesel et al.
6,200,338 B1 3/2001 Solomon et al.
6,204,203 B1 3/2001 Narwankar et al.
6,208,843 B1 3/2001 Huang et al.
6,214,629 B1 4/2001 Freitag et al.
6,222,489 B1 4/2001 Tsuru et al.
6,226,082 B1 5/2001 Roe
6,244,776 B1 6/2001 Wiley
6,261,065 B1 7/2001 Nayak et al.
6,262,798 B1 7/2001 Shepherd et al.
6,266,020 B1 7/2001 Chang
6,270,455 B1 8/2001 Brown
6,271,045 B1 8/2001 Douglas et al.
6,280,381 B1 8/2001 Malin et al.
6,285,448 B1 9/2001 Kunstner
6,300,894 B1 10/2001 Lynch et al.
6,309,370 B1 10/2001 Haim et al.
6,312,888 B1 11/2001 Wong et al.
6,320,547 B1 11/2001 Fathy et al.
6,323,549 B1 11/2001 deRochemont et al.
6,334,851 B1 1/2002 Hayes et al.
6,363,609 B1 4/2002 Pickren
6,375,627 B1 4/2002 Mauze et al.
6,375,638 B2 4/2002 Nason et al.
6,379,301 B1 4/2002 Worthington et al.
6,402,689 B1 6/2002 Scarantino et al.
6,470,279 B1 10/2002 Samsoondar
6,474,219 B2 11/2002 Klitmose et al.
6,475,196 B1 11/2002 Vachon
6,477,065 B2 11/2002 Parks
6,477,901 B1 11/2002 Tadigadapa et al.
6,484,044 B1 11/2002 Lilienfeld-Toal
6,485,461 B1 11/2002 Mason et al.
6,485,462 B1 11/2002 Kriesel
6,491,656 B1 12/2002 Morris
6,492,949 B1 12/2002 Breglia et al.
6,496,149 B1 12/2002 Birnbaum et al.
6,501,415 B1 12/2002 Viana et al.
6,512,937 B2 1/2003 Blank et al.
6,520,936 B1 2/2003 Mann
6,525,509 B1 2/2003 Petersson et al.
6,527,744 B1 3/2003 Kriesel et al.

(56) References Cited

U.S. PATENT DOCUMENTS 6,528,809 B1 3/2003 Thomas et al.
6,537,249 B2 3/2003 Kriesell et al.
6,540,260 B1 4/2003 Tan
6,540,672 B1 4/2003 Simonsen et al.
6,541,820 B1 4/2003 Bol
6,544,212 B2 4/2003 Galley et al.
6,546,268 B1 4/2003 Ishikawa et al.
6,546,269 B1 4/2003 Kurnik
6,552,693 B1 4/2003 Leisten
6,553,841 B1 4/2003 Blouch
6,554,798 B1 4/2003 Mann et al.
6,556,850 B1 4/2003 Braig et al.
6,558,351 B1 5/2003 Steil et al.
6,559,735 B1 5/2003 Hoang et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,115 B1 5/2003 Barker et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,583,699 B2 6/2003 Yokoyama
6,595,956 B1 7/2003 Gross et al.
6,605,151 B1 8/2003 Wessels et al.
6,611,419 B1 8/2003 Chakravorty
6,618,603 B2 9/2003 Varalli et al.
6,620,750 B2 9/2003 Kim et al.
6,633,772 B2 10/2003 Ford et al.
6,635,958 B2 10/2003 Bates et al.
6,639,556 B2 10/2003 Baba
6,642,908 B2 11/2003 Pleva et al.
6,645,142 B2 11/2003 Braig et al.
6,650,303 B2 11/2003 Kim et al.
6,653,091 B1 11/2003 Dunn et al.
6,656,158 B2 12/2003 Mahoney et al.
6,662,030 B2 12/2003 Khalil et al.
6,669,663 B1 12/2003 Thompson
6,670,497 B2 12/2003 Tashino et al.
6,678,542 B2 1/2004 Braig et al.
6,680,700 B2 1/2004 Hilgers
6,683,576 B2 1/2004 Achim
6,686,406 B2 2/2004 Tomomatsu et al.
6,690,336 B1 2/2004 Leisten et al.
6,697,605 B1 2/2004 Atokawa et al.
6,699,218 B2 3/2004 Flaherty et al.
6,699,221 B2 3/2004 Vaillancourt
6,718,189 B2 4/2004 Rohrscheib et al.
6,720,926 B2 4/2004 Killen et al.
6,721,582 B2 4/2004 Trepagnier et al.
6,723,072 B2 4/2004 Flaherty et al.
6,727,785 B2 4/2004 Killen et al.
6,728,560 B2 4/2004 Kollias et al.
6,731,244 B2 5/2004 Killen et al.
6,731,248 B2 5/2004 Killen et al.
6,733,890 B2 5/2004 Imanaka et al.
6,740,059 B2 5/2004 Flaherty
6,740,072 B2 5/2004 Starkweather et al.
6,741,148 B2 5/2004 Killen et al.
6,742,249 B2 6/2004 deRochemont et al.
6,743,744 B1 6/2004 Kim et al.
6,750,740 B2 6/2004 Killen et al.
6,750,820 B2 6/2004 Killen et al.
6,751,490 B2 6/2004 Esenaliev et al.
6,753,745 B2 6/2004 Killen et al.
6,753,814 B2 6/2004 Killen et al.
6,758,835 B2 7/2004 Close et al.
6,762,237 B2 7/2004 Glatkowski et al.
6,780,156 B2 8/2004 Haueter et al.
6,787,181 B2 9/2004 Uchiyama et al.
6,791,496 B1 9/2004 Killen et al.
6,810,290 B2 10/2004 Lebel et al.
6,826,031 B2 11/2004 Nagai et al.
6,830,623 B2 12/2004 Hayashi et al.
6,837,858 B2 1/2005 Cunningham et al.
6,837,988 B2 1/2005 Leong et al.
6,846,288 B2 1/2005 Nagar et al.
6,853,288 B2 2/2005 Ahn et al.
6,858,892 B2 2/2005 Yamagata
6,862,534 B2 3/2005 Sterling et al.
6,864,848 B2 3/2005 Sievenpiper
6,865,408 B1 3/2005 Abbink et al.
6,871,396 B2 3/2005 Sugaya et al.
6,878,871 B2 4/2005 Scher et al.
6,883,778 B1 4/2005 Newton et al.
6,890,291 B2 5/2005 Robinson et al.
6,905,989 B2 6/2005 Ellis et al.
6,906,674 B2 6/2005 McKinzie, III et al.
6,914,566 B2 7/2005 Beard
6,919,119 B2 7/2005 Kalkan et al.
6,928,298 B2 8/2005 Furutani et al.
6,936,029 B2 8/2005 Mann et al.
6,943,430 B2 9/2005 Kwon
6,943,731 B2 9/2005 Killen et al.
6,949,081 B1 9/2005 Chance
6,958,809 B2 10/2005 Sterling et al.
6,963,259 B2 11/2005 Killen et al.
6,989,891 B2 1/2006 Braig et al.
6,990,366 B2 1/2006 Say et al.
7,002,436 B2 2/2006 Ma et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,047,637 B2 5/2006 deRochemont et al.
7,060,059 B2 6/2006 Keith et al.
7,060,350 B2 6/2006 Takaya et al.
7,061,593 B2 6/2006 Braig et al.
7,096,124 B2 8/2006 Sterling et al.
7,115,205 B2 10/2006 Robinson et al.
7,116,949 B2 10/2006 Irie et al.
7,128,727 B2 10/2006 Flaherty et al.
7,137,694 B2 11/2006 Ferran et al.
7,139,593 B2 11/2006 Kavak et al.
7,139,598 B2 11/2006 Hull et al.
7,144,384 B2 12/2006 Gorman et al.
7,160,272 B1 1/2007 Eyal et al.
7,171,252 B1 1/2007 Scarantino et al.
7,190,988 B2 3/2007 Say et al.
7,204,823 B2 4/2007 Estes et al.
7,230,316 B2 6/2007 Yamazaki et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,291,782 B2 11/2007 Sager et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,405,698 B2 7/2008 de Rochemont
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,522,124 B2 4/2009 Smith et al.
7,547,281 B2 6/2009 Hayes et al.
7,553,512 B2 6/2009 Kodas et al.
7,564,887 B2 7/2009 Wang et al.
7,569,030 B2 8/2009 Lebel et al.

(56) References Cited

U.S. PATENT DOCUMENTS 7,595,623 B2 9/2009 Bennett
7,608,042 B2 10/2009 Goldberger et al.
7,651,845 B2 1/2010 Doyle, III et al.
7,652,901 B2 1/2010 Kirchmeier et al.
7,680,529 B2 3/2010 Kroll
7,714,794 B2 5/2010 Tavassoli Hozouri
7,734,323 B2 6/2010 Blomquist et al.
7,763,917 B2 7/2010 de Rochemont
7,766,829 B2 8/2010 Sloan et al.
7,771,391 B2 8/2010 Carter
7,785,258 B2 8/2010 Braig et al.
7,806,854 B2 10/2010 Damiano et al.
7,806,886 B2 10/2010 Kanderian, Jr. et al.
7,812,774 B2 10/2010 Friman et al.
7,918,825 B2 4/2011 OConnor et al.
7,946,985 B2 5/2011 Mastrototaro et al.
7,972,296 B2 7/2011 Braig et al.
8,066,805 B2 11/2011 Zurcher et al.
8,069,690 B2 12/2011 DeSantolo et al.
8,114,489 B2 2/2012 Nemat-Nasser et al.
8,178,457 B2 5/2012 de Rochemont
8,193,873 B2 6/2012 Kato et al.
8,221,345 B2 7/2012 Blomquist
8,251,907 B2 8/2012 Sterling et al.
8,267,921 B2 9/2012 Yodfat et al.
8,350,657 B2 1/2013 deRochemont
8,354,294 B2 1/2013 de Rochemont et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
8,547,239 B2 10/2013 Peatfield et al.
8,593,819 B2 11/2013 de Rochemont
8,597,274 B2 12/2013 Sloan et al.
8,622,988 B2 1/2014 Hayter
8,715,839 B2 5/2014 de Rochemont
8,810,394 B2 8/2014 Kalpin
8,939,935 B2 1/2015 OConnor et al.
9,061,097 B2 6/2015 Holt et al.
9,171,343 B1 10/2015 Fischell et al.
9,180,244 B2 11/2015 Anderson et al.
9,192,716 B2 11/2015 Jugl et al.
9,233,204 B2 1/2016 Booth et al.
9,402,950 B2 8/2016 Dilanni et al.
9,486,571 B2 11/2016 Rosinko
9,520,649 B2 12/2016 de Rochemont
9,579,456 B2 2/2017 Budiman et al.
9,656,017 B2 5/2017 Greene
9,743,224 B2 8/2017 San Vicente et al.
9,857,090 B2 1/2018 Golden et al.
9,907,515 B2 3/2018 Doyle, III et al.
9,980,140 B1 5/2018 Spencer et al.
9,984,773 B2 5/2018 Gondhalekar et al.
10,248,839 B2 4/2019 Levy et al.
10,335,464 B1 7/2019 Michelich et al.
10,583,250 B2 3/2020 Mazlish et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0048969 A1 12/2001 Constantino et al.
2001/0051377 A1 12/2001 Hammer et al.
2001/0053895 A1 12/2001 Vaillancourt
2001/0056258 A1 12/2001 Evans
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0047768 A1 4/2002 Duffy
2002/0070983 A1 6/2002 Kozub et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2002/0173769 A1 11/2002 Gray et al.
2002/0190818 A1 12/2002 Endou et al.
2003/0023148 A1 1/2003 Lorenz et al.
2003/0034124 A1 2/2003 Sugaya et al.
2003/0040715 A1 2/2003 DAntonio et al.
2003/0050621 A1 3/2003 Lebel et al.
2003/0060692 A1 3/2003 L. Ruchti et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0122647 A1 7/2003 Ou
2003/0130616 A1 7/2003 Steil et al.
2003/0135388 A1 7/2003 Martucci et al.
2003/0144582 A1 7/2003 Cohen et al.
2003/0148024 A1 8/2003 Kodas et al.
2003/0163097 A1 8/2003 Fleury et al.
2003/0170436 A1 9/2003 Sumi et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2003/0221621 A1 12/2003 Pokharna et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064088 A1 4/2004 Gorman et al.
2004/0064259 A1 4/2004 Haaland et al.
2004/0068224 A1 4/2004 Alfred, Jr. et al.
2004/0069044 A1 4/2004 Lavi et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Ebel et al.
2005/0075624 A1 4/2005 Miesel
2005/0105095 A1 5/2005 Pesach et al.
2005/0134609 A1 6/2005 Yu
2005/0137573 A1 6/2005 McLaughlin
2005/0171503 A1 8/2005 Van Den Berghe et al.
2005/0182306 A1 8/2005 Sloan
2005/0182366 A1 8/2005 Vogt et al.
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0262451 A1 11/2005 Remignanti et al.
2005/0272640 A1 12/2005 Doyle, III et al.
2005/0277912 A1 12/2005 John
2006/0009727 A1 1/2006 OMahony et al.
2006/0041229 A1 2/2006 Garibotto et al.
2006/0079765 A1 4/2006 Neer et al.
2006/0079809 A1 4/2006 Goldberger et al.
2006/0086994 A1 4/2006 Viefers et al.
2006/0100494 A1 5/2006 Kroll

(56) References Cited

U.S. PATENT DOCUMENTS

2006/0134323 A1 6/2006 OBrien
2006/0134491 A1 6/2006 Hilchenko et al.
2006/0167350 A1 7/2006 Monfre et al.
2006/0173406 A1 8/2006 Hayes et al.
2006/0178633 A1 8/2006 Garibotto et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0100635 A1 5/2007 Mahajan et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0166453 A1 7/2007 Van Duren et al.
2007/0173761 A1 7/2007 Kanderian et al.
2007/0173974 A1 7/2007 Lin et al.
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0259768 A1 11/2007 Kear et al.
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051738 A1 2/2008 Griffin
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0097289 A1 4/2008 Steil et al.
2008/0114304 A1 5/2008 Nalesso et al.
2008/0132880 A1 6/2008 Buchman
2008/0160492 A1 7/2008 Campbell et al.
2008/0161664 A1 7/2008 Mastrototaro et al.
2008/0172026 A1 7/2008 Blomquist
2008/0172028 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2009/0326472 A1 12/2009 Carter
2010/0017141 A1 1/2010 Campbell et al.
2010/0036326 A1 2/2010 Matusch
2010/0057042 A1 3/2010 Hayter
2010/0064243 A1 3/2010 Buck et al.
2010/0077198 A1 3/2010 Buck et al.
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0185183 A1 7/2010 Alme et al.
2010/0211003 A1 8/2010 Sundar et al.
2010/0228110 A1 9/2010 Tsoukalis
2010/0241066 A1 9/2010 Hansen et al.
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0049394 A1 3/2011 de Rochemont
2011/0054390 A1 3/2011 Searle et al.
2011/0054399 A1 3/2011 Chong et al.
2011/0065224 A1 3/2011 Bollman et al.
2011/0071765 A1 3/2011 Yodfat et al.
2011/0124996 A1 5/2011 Reinke et al.
2011/0144586 A1 6/2011 Michaud et al.
2011/0160652 A1 6/2011 Yodfat et al.
2011/0178472 A1 7/2011 Cabiri
2011/0190694 A1 8/2011 Lanier, Jr. et al.
2011/0202005 A1 8/2011 Yodfat et al.
2011/0218495 A1 9/2011 Remde
2011/0230833 A1 9/2011 Andman et al.
2011/0251509 A1 10/2011 Beyhan et al.
2011/0313680 A1 12/2011 Doyle et al.
2011/0316562 A1 12/2011 Cefai et al.
2012/0003935 A1 1/2012 Lydon et al.
2012/0010594 A1 1/2012 Holt et al.
2012/0030393 A1 2/2012 Ganesh et al.
2012/0035543 A1* 2/2012 Kamen ................. A61M 5/385 604/113
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1 5/2012 Atlas et al.
2012/0124521 A1 5/2012 Guo
2012/0136336 A1 5/2012 Mastrototaro et al.
2012/0150446 A1 6/2012 Chang et al.
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0250449 A1 10/2012 Nakano
2012/0271655 A1 10/2012 Knobel et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0158503 A1 6/2013 Kanderian, Jr. et al.

(56) References Cited

U.S. PATENT DOCUMENTS

2013/0172695 A1 7/2013 Nielsen et al.
2013/0172710 A1 7/2013 Mears et al.
2013/0178791 A1 7/2013 Javitt
2013/0231642 A1 9/2013 Doyle et al.
2013/0245545 A1 9/2013 Arnold et al.
2013/0253472 A1 9/2013 Cabiri
2013/0261406 A1 10/2013 Rebec et al.
2013/0296792 A1 11/2013 Cabiri
2013/0296823 A1 11/2013 Melker et al.
2013/0298080 A1 11/2013 Griffin et al.
2013/0317753 A1 11/2013 Kamen et al.
2013/0332874 A1 12/2013 Rosinko et al.
2013/0338576 A1 12/2013 OConnor et al.
2013/0346858 A1 12/2013 Neyrinck
2014/0005633 A1 1/2014 Finan
2014/0018730 A1 1/2014 Muller-Pathle
2014/0032549 A1 1/2014 McDaniel et al.
2014/0046288 A1 2/2014 Geipel et al.
2014/0066886 A1 3/2014 Roy et al.
2014/0074033 A1 3/2014 Sonderegger et al.
2014/0088428 A1 3/2014 Yang et al.
2014/0108046 A1 4/2014 Cabrera et al.
2014/0121635 A1 5/2014 Hayter
2014/0128839 A1 5/2014 Dilanni et al.
2014/0129951 A1 5/2014 Amin et al.
2014/0135880 A1 5/2014 Baumgartner et al.
2014/0142508 A1 5/2014 Dilanni et al.
2014/0146202 A1 5/2014 Boss et al.
2014/0171901 A1 6/2014 Langsdorf et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1 9/2014 Finan et al.
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0025503 A1 1/2015 Searle et al.
2015/0041498 A1 2/2015 Kakiuchi et al.
2015/0120317 A1 4/2015 Mayou et al.
2015/0134265 A1 5/2015 Kohlbrecher et al.
2015/0134353 A1 5/2015 Ferrell et al.
2015/0165119 A1 6/2015 Palerm et al.
2015/0173674 A1 6/2015 Hayes et al.
2015/0193585 A1 7/2015 Sunna
2015/0202386 A1 7/2015 Brady et al.
2015/0205509 A1 7/2015 Scriven et al.
2015/0205511 A1 7/2015 Vinna et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0301691 A1 10/2015 Qin
2015/0306314 A1 10/2015 Doyle et al.
2015/0331995 A1 11/2015 Zhao et al.
2015/0351671 A1 12/2015 Vanslyke et al.
2015/0356250 A1 12/2015 Polimeni
2015/0366945 A1 12/2015 Greene
2016/0015891 A1 1/2016 Papiorek
2016/0019352 A1 1/2016 Cohen et al.
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0220181 A1 8/2016 Rigooard et al.
2016/0228641 A1 8/2016 Gescheit et al.
2016/0243318 A1 8/2016 Despa et al.
2016/0256087 A1 9/2016 Doyle et al.
2016/0259889 A1 9/2016 Murtha et al.
2016/0287512 A1 10/2016 Cooper et al.
2016/0302054 A1 10/2016 Kimura et al.
2016/0331310 A1 11/2016 Kovatchev
2016/0354543 A1 12/2016 Cinar et al.
2017/0021096 A1 1/2017 Cole et al.
2017/0049386 A1 2/2017 Abraham et al.
2017/0131887 A1 5/2017 Kim et al.
2017/0143899 A1 5/2017 Gondhalekar et al.
2017/0143900 A1 5/2017 Rioux et al.
2017/0156682 A1 6/2017 Doyle et al.
2017/0173261 A1 6/2017 O'Connor et al.
2017/0189625 A1 7/2017 Cirillo et al.
2017/0216523 A1* 8/2017 Neftel .................. A61M 5/172
2017/0216524 A1 8/2017 Haider et al.
2017/0239415 A1 8/2017 Hwang et al.
2017/0281877 A1 10/2017 Marlin et al.
2017/0296746 A1 10/2017 Chen et al.
2017/0311903 A1 11/2017 Davis et al.
2017/0348482 A1 12/2017 Duke et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0277253 A1 9/2018 Gondhalekar et al.
2018/0289891 A1 10/2018 Finan et al.
2018/0296757 A1 10/2018 Finan et al.
2018/0307515 A1 10/2018 Meller et al.
2018/0342317 A1 11/2018 Skirble et al.
2018/0369479 A1 12/2018 Hayter et al.
2019/0076600 A1 3/2019 Grosman et al.
2019/0095052 A1 3/2019 De Wever et al.
2019/0132801 A1 5/2019 Kamath et al.
2019/0184091 A1 6/2019 Sjolund et al.
2019/0240403 A1 8/2019 Palerm et al.
2019/0290844 A1 9/2019 Monirabbasi et al.
2019/0321545 A1 10/2019 Saint
2019/0336683 A1 11/2019 O'Connor et al.
2019/0336684 A1 11/2019 O'Connor et al.
2019/0348157 A1 11/2019 Booth et al.
2019/0374714 A1 12/2019 Rioux et al.
2020/0001006 A1 1/2020 Pizzochero et al.
2020/0046268 A1 2/2020 Patek et al.
2020/0101222 A1 4/2020 Lintereur et al.
2020/0101223 A1 4/2020 Lintereur et al.
2020/0101225 A1 4/2020 O'Connor et al.
2020/0113515 A1 4/2020 O'Connor et al.
2020/0219625 A1 7/2020 Kahlbaugh
2020/0342974 A1 10/2020 Chen et al.
2021/0050085 A1 2/2021 Hayter et al.
2021/0098105 A1 4/2021 Lee et al.
2021/0400133 A1* 12/2021 Coppin ................. H04W 4/029
2022/0023536 A1 1/2022 Graham et al.

FOREIGN PATENT DOCUMENTS

CN 1297140 A 5/2001
CN 101208699 A 6/2008
DE 4200595 A1 7/1993
DE 19756872 A1 7/1999
EP 0026056 A1 4/1981
EP 0341049 A2 11/1989
EP 0496305 A2 7/1992
EP 0549341 A1 6/1993
EP 0867196 A2 9/1998
EP 0939451 A1 9/1999
EP 1177802 A1 2/2002
EP 1376759 A2 1/2004
EP 1491144 A1 12/2004
EP 0801578 B1 7/2006

(56) References Cited

FOREIGN PATENT DOCUMENTS

| | | | |
|---|---|---|---|
| EP | 2139382 | A1 | 1/2010 |
| EP | 2397181 | A1 | 12/2011 |
| EP | 2468338 | A1 | 6/2012 |
| EP | 2666520 | A1 | 11/2013 |
| EP | 2695573 | A2 | 2/2014 |
| EP | 2703024 | A1 | 3/2014 |
| EP | 2830499 | A1 | 2/2015 |
| EP | 2943149 | A1 | 11/2015 |
| EP | 3177344 | A1 | 6/2017 |
| EP | 3193979 | A1 | 7/2017 |
| EP | 3314548 | A1 | 5/2018 |
| EP | 1571582 | B1 | 4/2019 |
| EP | 2897071 | B1 | 5/2019 |
| EP | 3607985 | A1 | 2/2020 |
| FR | 2096275 | A5 | 2/1972 |
| GB | 1125897 | A | 9/1968 |
| GB | 2443261 | A | 4/2008 |
| JP | 51125993 | A | 11/1976 |
| JP | 02131777 | A | 5/1990 |
| JP | 2005326943 | A | 11/2005 |
| JP | 2004283378 | A | 10/2007 |
| JP | 2008513142 | A | 5/2008 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 200048112 | A2 | 9/1968 |
| WO | 8606796 | A1 | 11/1986 |
| WO | 9800193 | A1 | 1/1998 |
| WO | 9855073 | A1 | 12/1998 |
| WO | 9910040 | A1 | 3/1999 |
| WO | 9910049 | A1 | 3/1999 |
| WO | 9956803 | A1 | 11/1999 |
| WO | 9962576 | A1 | 12/1999 |
| WO | 0030705 | A1 | 6/2000 |
| WO | 200032258 | A1 | 6/2000 |
| WO | 0172354 | A2 | 10/2001 |
| WO | 2001078812 | A1 | 10/2001 |
| WO | 2002015954 | A1 | 2/2002 |
| WO | 0226282 | A2 | 4/2002 |
| WO | 2002043866 | A2 | 6/2002 |
| WO | 2002076535 | A1 | 10/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2003097133 | A1 | 11/2003 |
| WO | 2004043250 | A1 | 5/2004 |
| WO | 2005110601 | A1 | 5/2004 |
| WO | 2004092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007066152 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009039203 | A2 | 3/2009 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010022069 | A2 | 2/2010 |
| WO | 2010053702 | A1 | 5/2010 |
| WO | 2010077279 | A1 | 7/2010 |
| WO | 2010132077 | A1 | 11/2010 |
| WO | 2010138848 | A1 | 12/2010 |
| WO | 2010139793 | A1 | 12/2010 |
| WO | 2010147659 | A2 | 12/2010 |
| WO | 2011031458 | A1 | 3/2011 |
| WO | 2011075042 | A1 | 6/2011 |
| WO | 2011095483 | A1 | 8/2011 |
| WO | 2011133823 | A1 | 10/2011 |
| WO | 2012045667 | A2 | 4/2012 |
| WO | 2012073032 | A1 | 6/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013050535 | A2 | 4/2013 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014029416 | A1 | 2/2014 |
| WO | 2014109898 | A1 | 7/2014 |
| WO | 2014110538 | A1 | 7/2014 |
| WO | 2014149357 | A1 | 9/2014 |
| WO | 2014179774 | A1 | 11/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015117082 | A1 | 8/2015 |
| WO | 2015117854 | A1 | 8/2015 |
| WO | 2015167201 | A1 | 11/2015 |
| WO | 2015177082 | A1 | 11/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017187177 | A1 | 11/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

(56) References Cited

OTHER PUBLICATIONS

European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al.: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, Nl, vol. 146, Jun. 1, 2017 (2017-06-01), pp. 125-131, XP085115607, Issn: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on 2022-06-06] chapter "Functioning of the Algorithm" chapter "Statistical Analysis" p. 1183, left-hand col. line 16- line 23.
Anonymous: "Kernel density estimation", Wikipedia, Nov. 13, 2020 (2020-11-13), pp. 1-12, XP055895569, Retrieved from the Internet: URL:https://en.wikipedia.org/w/index.php? title=Kernel_density_estimation&oldid=988508333 [retrieved on 2022-06-06].
Anonymous: "openaps / oref0 /lib/determine-basal-js", openaps repository, Nov. 9, 2019 (2019-11-09), pp. 1-17, XP055900283, Retrieved from the Internet: URL:https://github.com/openaps/oref0/blob/ master/lib/determine-basal/determine-basal.js [retrieved on 2022-06-06] line 116 - line 118, line 439 - line 446.
Anonymous: "AndroidAPS screens", AndroidAPS documentation, Oct. 4, 2020 (2020-10-04), pp. 1-12, XP055894824, Retrieved from the Internet: URL:https://github.com/openaps/AndroidAPSdocs/ blob/25d8acf8b28262b411b34f416f173ac0814d7e14/docs/EN/Getting-Started/Screenshots.md [retrieved on 2022-06-06].
Kozak Milos et al.: "Issue #2473 of AndroidAPS", MilosKozak / AndroidAPS Public repository, Mar. 4, 2020 (2020-03-04), pp. 1-4, XP055900328, Retrieved from the Internet: URL:https://github.com/MilosKozak/AndroidAPS/ Issues/2473 [retrieved on 2022-06-06].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G .; Machine Learning for Physiological Time Series: Representing and Controlling Blood Glucose for Diabetes Management; University of Michigan. ProQuest Dissertations Publishing, 2020. 28240142. (Year: 2020).
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

(56) References Cited

OTHER PUBLICATIONS

Gorke, A "Microbial Contamination of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS. 247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved on Dec. 29, 2010 from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech, vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Andrenko et al., "EM Analysis of PBG Substrate Microstrip Circuits for Integrated Transmitter Front End" MMET Proceedings, 295-297 (2000).
Bardi et al., "Plane Wave Scattering From Frequency-Selective Surfaces by the Finite-Element Method" IEEE Transactions on Magnetics 38(2):641-644 (2002).
Chappell et al., "Composite Metamaterial Systems for Two-Dimensional Periodic Structures" IEEE, 3840387 (2002).
Cheng et al., "Preparation and Characterization of (Ba, Sr) TiO3 thin films using interdigitial electrodes" Microelectronic Engineering, 66:872-879 (2003).
Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).
Diaz et al., "Magnetic Loading of Antificial Magnetic Conductors for Bandwidth Enhancement" IEEE, 431-434 (2003).
Hansen "Effect of a High-Impedance Screen on a Dipole Antenna" IEEE Antennas and Wireless Propagation Letter, 1:46-49 (2002).

(56) References Cited

OTHER PUBLICATIONS

Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).
Kern et al., "Active Negative Impedance Loaded EBG Structures for the Realization of Ultra-Wideband Artificial Magnetic Conductors" IEEE, 427-430 (2003).
Kern et al., "The Synthesis of Metamaterial Ferrities for RF Applications Using Electromagnetic Bandgap Structures" IEEE, 497-500 (2003).
Kern et al., "Ultra-thin Electromagnetic Bandgap Absorbers Synthesized via Genetic Algorithms" IEEE, 1119-1122 (2003).
Kuhn et al., "Characterization of novel mono- and bifacially active semi-transparent crystalline silicon solar cells" IEEE Transactions on Electron Devices, 46(10): 2013-2017 (1999).
Kretly et al., "The Influence of the Height Variation on the Frequency Bandgap in an AMC, Artificial magnetic Conductor for Wireless Applications: an EM Experimental Design Approach" Proceedings Sbmo/IEEE MTT-S IMOC, 219-223 (2003).
Lee et al., "Investigation of Electromagnetic Bandgap (EBG) Structures for Antenna Pattern Control" IEEE, 1115-1118 (2003).
Mckinzie III et al., "Mitigation of Multipath Through the Use of an Artificial Magnetic Conductor for Precision CPS Surveying Antennas" IEEE, 640-643; Date of Conference: Jun. 16-21, 2002.
Monorciho et al., "Synthesis of Artificial Magnetic Conductors by Using Multilatered Frequency Selective Surfaces" IEEE Antennas and Wireless Propagation Letters, 1:196-1999 (2002).
Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).
Pontes et al., "Study of the dielectric and ferroelectric properties of chemically processed BaxSr1—xTiO3 thin films" Thin Solid Films, 386(2)91-98 (2001).
Rogers et al., "AMCs Comprised of Interdigital Capacitor FSS Layers Enable Lower Cost Applications" IEEE, 411-414 (2003).
Sievenpiper et al., "Two-Dimensional Beam Steering Using an Electrically Tunable Impedance Surface" IEEE Transactions on Antennas and Propagation, 51(10):2713-2722(2003).
Sun et al., "Efficiency of Various Photonic Bandgap (PBG) Structures" 3rd Int'l. Conf. on Microwave and Millimeter Wave Technology Proceedings, 1055-1058 (2002).
Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).
Vest "Metallo-organic decomposition (MOD) processing of ferroelectric and electro-optic films: A review" Ferroelectrics, 102(1):53-68 (1990).
Viviani et al., "Positive Temperature Coefficient of Electrical Resistivity below 150k of Barium Strontium Titanate" J. Amer. Ceram. Soc. 87(4): 756-758 (2004).
Weily et al., "Antennas Based on 2-D and 3-D Electromagnetic Bandgap Materials" IEEE, 847-850 (2003).
Yang et al., "Surface Waves of Printed Antennas on Planar Artificial Periodic Dielectric Structures" IEEE Transactions on Antennas and Propagation 49(3): 444-450 (2001).
Zhang et al., "Planar Artificial magnetic Conductors and Patch Antennas" IEEE Transactions on Antennas and Propagation, 51(10):2704-2712 (2003).
Ziroff et al., "A Novel Approach for LTCC Packaging Using a PBG Structure for Shielding and Package Mode Suppression" 33rd European Microwave Conference—Munich 419-422 (2003).
International Search Report and Written Opinion for Application No. PCT/US17/61336, mailed on Jan. 25, 2018, 9 pages.
"Graph Chart." iconfinder.com. Aug. 15, 2016. Accessed Apr. 21, 2020. Available online at URL: https://www.confinder.com/iconsets/graph-chart-2>.
"Circular Progress Indicator Component for React." reactscript.com. Dec. 2, 2016. Accessed Sep. 9, 2020. Available online at URL: <http://reactscripts.com/circular-progress-indicator-component-react/>.
Kruska, Michal. "Circle progress bar." dribbble.com. Oct. 18, 2012. Accessed Apr. 21, 2020. Available online at URL: <https://dribbble.com/shots/775718-Circle-progress-bar>.
"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-kamarin-forms>.
International Search Report and Written Opinion for Application No. PCT/US2021/047685 mailed on Dec. 6, 2021, 15 pages.
"Circular Loader." dribbble.com. Nov. 19, 2015. Accessed Jul. 24, 2019. Available online at URL: https://dribbble.com/shots/2362441-Circular-Loader (Year: 2015).
"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- -knobs-range-slider> (Year: 2015).
"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).
"Tick and cross circle shape icon . . . " depositphotos.com. Aug. 27, 2016. Accessed Feb. 1, 2019. Available online at URL:<https://depositphotos.com/121291612/stock-illustration-tick-and-cross-circle-shape.html> (Year: 2016).
"Vector-Vector Illustration of Preloader / Buffer Shapes, or Dials with Knobs." 123rf.com. Date not available. Accessed Oct. 25, 2018. Available online at URL: <https://www.123rf.com/photo_37292689_stock-vector-vector-illustration- -of-preloader-buffer-shapes-or-dials-with-knobs.html> (Year: N/A).
Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).
Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/how-to-use-the-new-features-in-ios-9-notes-app.html.
International Search Report and Written Opinion for the International Patent Application No. PCT/US21/064056, mailed Apr. 4, 2022, 12 pages.
International Search Report and Written Opinion for the International Patent Application No. PCT/US21/064170, mailed Apr. 20, 2022, 12 pages.
Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.
Team Section—Qonto, by Christophe Kerebel, dated Dec. 12, 2018, dribbble.com [online]. Retrieved Jul. 1, 2022 from Internet <URL: https://dribbble.com/shots/5676730-Team-Section-Qonto> (Year: 2018).
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

(56) References Cited

OTHER PUBLICATIONS

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.

* cited by examiner

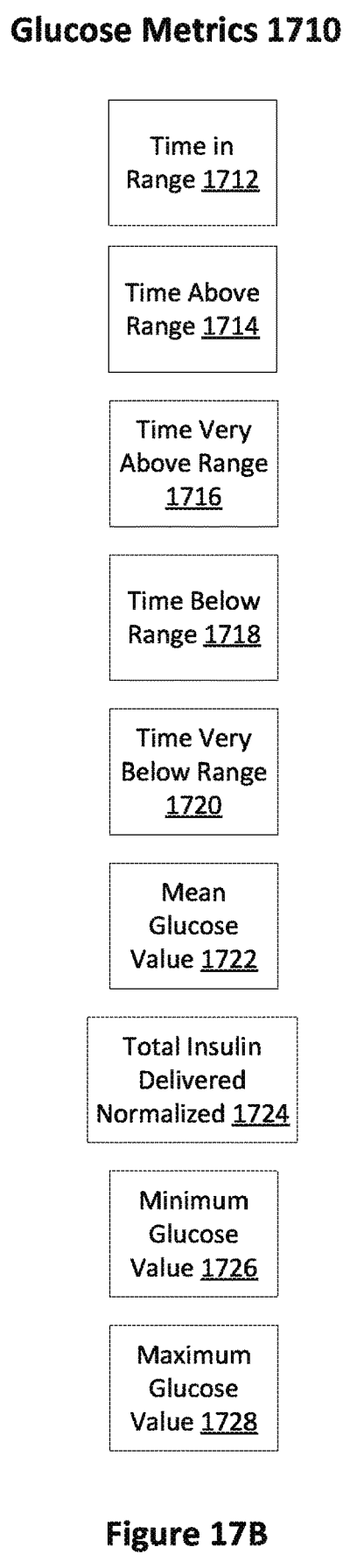

Glucose Metrics 1710

Time in Range 1712

Time Above Range 1714

Time Very Above Range 1716

Time Below Range 1718

Time Very Below Range 1720

Mean Glucose Value 1722

Total Insulin Delivered Normalized 1724

Minimum Glucose Value 1726

Maximum Glucose Value 1728

Figure 17B

ADAPTATION OF A MEDICAMENT DELIVERY DEVICE TO CHANGING ENVIRONMENTAL CONDITIONS

RELATED APPLICATIONS

This application claims the benefit of U.S. Provisional Patent Application No. 63/335,493, filed Apr. 27, 2022, the entire contents of which are incorporated herein by reference in their entirety.

BACKGROUND

A conventional medicament delivery device, such as an insulin pump, may be affected by changing environmental conditions. For instance, changes in ambient pressure may affect operation of the conventional medicament delivery device. One common place where ambient pressure may differ substantially from normal is when a user wearing the conventional medicament delivery device is on an airplane flight.

Variations in ambient air pressure may affect the quantity of medicament that is delivered by a conventional medicament delivery device. In low ambient air pressure environments, the conventional medicament delivery device may deliver an excessive amount of medicament to the user. This may be due, at least in part, to air bubbles being released from the medicament solution that cause over-delivery of the medicament to the user. Passengers in planes typically are in a low ambient air pressure environment during a flight. Hence, when a user is on a plane, the user is at risk of receiving an excessive dosage of medicament.

Air flights may also be subject to periods of increased acceleration, such as during takeoff, and increased deceleration, such as during landing. Delivery of a medicament by a conventional medicament delivery device during such periods may be problematic as sharp pressure changes may arise during such periods as well as possible device transients and/or adapting human physiological responses to acceleration/pressure changes. For example, there may be flow anomalies caused by the acceleration/pressure changes. The acceleration/pressure changes may cause increased mechanical vibrations that may affect medicament delivery. Still further, physiological responses to acceleration by the user, such as an elevated heart rate, heart rate variability being reduced due to stress and decreases in arterial oxygen saturation and arterial blood pressure, may affect the response of a user to medicament delivery at such times of acceleration changes. Hence, there is a risk of over-delivery or under-delivery of the medicament during such periods, depending on whether the ambient air pressure decreases or increases.

Low ambient air pressure may also pose a problem in environments that are at a high altitude, such as when a user is travelling through or staying in a mountainous region. The ambient air pressure is lower at altitude. Thus, a medicament delivery device may over-deliver the medicament when the user is at altitude. Yet another situation is when a user is scuba diving where the ambient pressure has increased. Also, when a user rides on a roller coaster or on other theme park ride with rapid accelerations/decelerations, drug delivery may be affected.

SUMMARY

In accordance with an inventive feature, a method is performed by a processor of an electronic device. The method includes determining with the processor that a user of a medicament delivery device is on an airplane flight and responsive to the determining, modifying with the processor delivery of medicament to the user by the medicament delivery device relative to delivery of the medicament to the user by the medicament delivery device when the user is not on an airplane flight to adapt for at least one environmental condition due to the user being on the airplane flight.

The at least one environmental condition may include a reduced air pressure, and a dosage of the medicament delivered by the medicament delivery device may be decreased responsive to the reduced air pressure. A rate of delivery of the medicament to the user by the medicament delivery device may be reduced responsive to the reduced air pressure. The rate of delivery may be reduced to suspend delivery of the medicament to the user by the medicament delivery device. The medicament may be insulin. The method may include displaying a request for the user to confirm that the user is on the airplane flight, and the determining may be based on receiving a response to the request where the response confirms that the user is on the airplane flight. The delivery of the medicament may deliver a bolus of medicament. The determining may be based on one or more of global positioning system (GPS) data, measurements by an accelerometer in the electronic device, an entry in an electronic calendar of the user, one or more pressure readings or network identification information for a network that is accessible to the electronic device.

In accordance with another inventive feature, a method is performed by a processor of an electronic device. The method includes receiving input from at least one sensor at the processor and based on the input, determining that a plane that a user is on is either taking off or landing. The method further includes altering delivery of a medicament by a medicament delivery device of the user responsive to determining that the plane the user is on is either taking off or landing.

The altering of delivery of the medicament may include prohibiting medicament delivery during taking off or landing of the plane. The at least one sensor may include an accelerometer in the electronic device. The determining that the plane that the user is on is taking off or landing may entail comparing the input received from the accelerometer with an accelerometer signature for taking off or an accelerometer signature for landing. The medicament may be insulin.

In accordance with an additional inventive feature, a method is performed by a processor of a handheld or wearable management device for managing a medicament delivery device of a user. The method includes, based on data received from at least one sensor, determining that a user is in flight on an airplane and adjusting settings of a control system of the medicament delivery device on the management device to modify control of delivery of the medicament by the medicament delivery device responsive to being in flight.

The at least one sensor may be an accelerometer. The accelerometer may be part of the management device. The at least one sensor may include a global positioning system (GPS) sensor. The adjusting of the settings may comprise at least one of reducing medicament delivery dosages, reducing a rate of deliveries of medicament by the medicament delivery device, or averaging basal medicament delivery rates over a period so as to deliver medicament at an average basal delivery rate while in flight. The method may further include, based on additional data received from the at least one sensor, determining that the plane has landed and modifying the settings of the control system based on the determining that the plane has landed. The modifying of the settings may include setting basal medicament deliveries at an in-flight average for a period.

BRIEF DESCRIPTION OF THE DRAWINGS

FIG. 17B depicts illustrative glucose metrics.

DETAILED DESCRIPTION

The exemplary embodiments may address the problems discussed above for conventional medicament delivery devices by adjusting settings for a medicament delivery device to account for altered environmental conditions, like reduced ambient air pressure or high acceleration or deceleration. The exemplary embodiments may detect the altered environmental conditions, like changed ambient air pressure, and may adjust settings for the medicament delivery device to compensate for the changed environmental conditions.

The exemplary embodiments may automatically detect events, such as takeoff and landing of a plane with a user of a medicament delivery device on board. The detection may rely on accelerometer output, calendar information for a user, geolocation information and/or network ID information to detect the events. Based on the detection of these events, the medicament delivery device may be switched into a flight mode. In the flight mode, medicament boluses may be reduced to nominal dosages, basal delivery rates may be modified and/or sample periods for sensors, like glucose monitors, may be shortened to sample sensor values more frequently. The exemplary embodiments may prohibit delivery of medicament during times of changing ambient air pressure to avoid over-delivering or under-delivering the medicament due to the ambient air pressure level or to safeguard against rapid accelerations/decelerations that may cause device transients and/or human physiological adaptations.

One touch bolus delivery may be provided in exemplary embodiments when in flight mode. A user interface may be provided that includes a button or other user interface element for the user to request a medicament bolus delivery. Upon selection of the user interface element by the user, a nominal dosage medicament bolus may be delivered to the user. The one touch bolus delivery avoids the difficulty of the user having to account for the environmental conditions in flight in choosing a bolus dosage. The one touch bolus delivery also relieves the user of the responsibility of determining the amount of carbohydrates in an in-flight meal while in a stressful environment.

The exemplary embodiments may provide a cool off period for a user of a medicament delivery device following extended flights that traverse multiple time zones. During the cool off period, the basal delivery rate of medicament may be set as an average basal delivery rate during the flight. The exemplary embodiments may provide the cool off period for a fixed period such as 3 days, which is generally accepted as a sufficient time for a user to acclimatize to the new destination time zone. After the expiration of the cool off period, the settings for basal medicament delivery may revert to the pre-flight "normal" settings.

Figure 1:
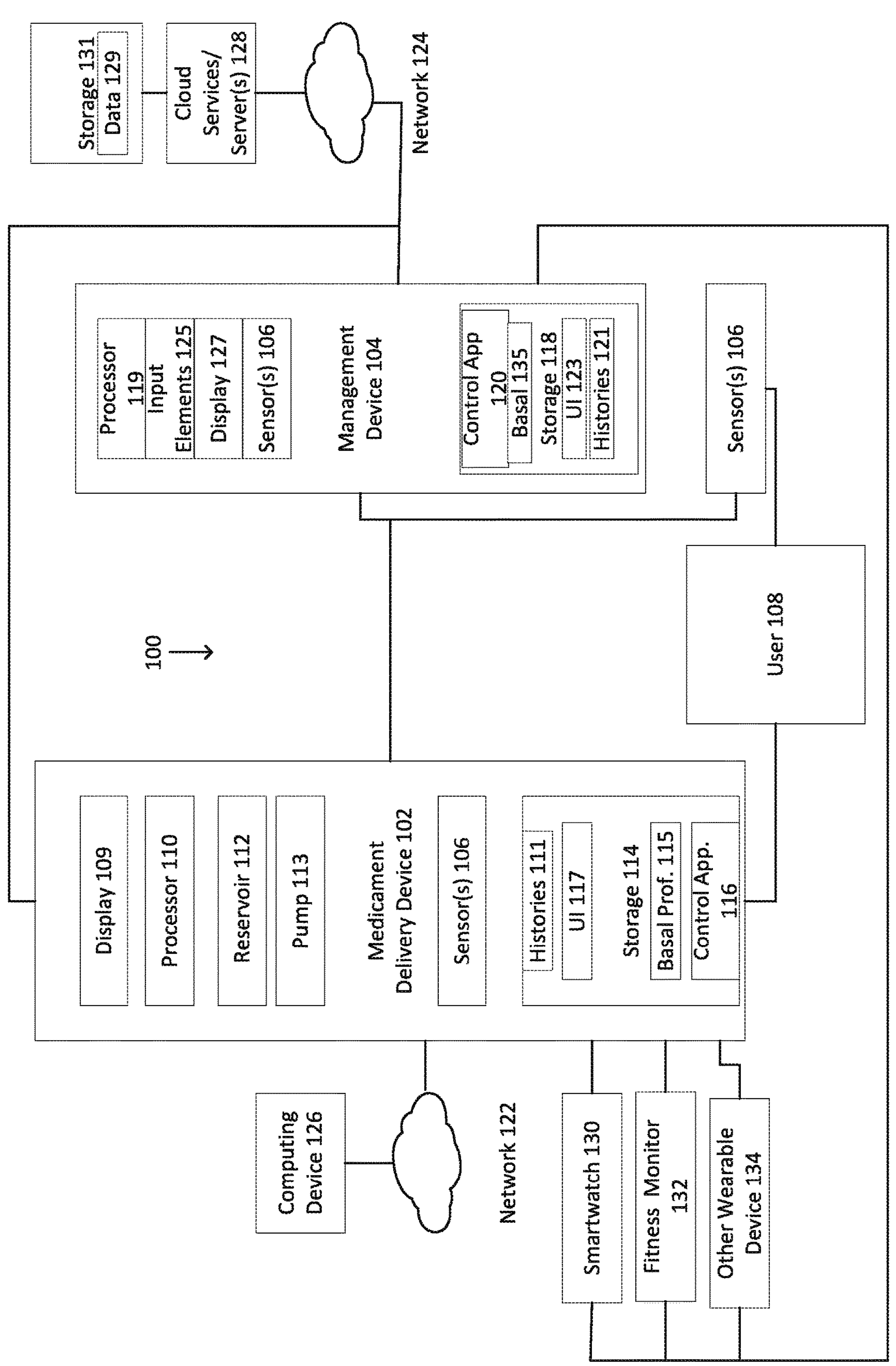
FIG. 1 depicts an illustrative medicament delivery system for exemplary embodiments.

FIG. 1 depicts an illustrative medicament delivery system 100 that is suitable for delivering a medicament to a user 108 in accordance with the exemplary embodiments. The medicament delivery system 100 includes a medicament delivery device 102. The medicament delivery device 102 may be a wearable device that is worn on the body of the user 108 or carried by the user 108. The medicament delivery device 102 may be directly coupled to the user 108 (e.g., directly attached to a body part and/or skin of the user 108 via an adhesive or the like) or carried by the user 108 (e.g., on a belt or in a pocket) with the medicament delivery device 102 being connected to an infusion site where the medicament is injected using a needle and/or cannula. In a preferred embodiment, a surface of the medicament delivery device 102 may include an adhesive to facilitate attachment to the user 108.

The medicament delivery device 102 may include a processor 110. The processor 110 may be, for example, a microprocessor, a logic circuit, a field programmable gate array (FPGA), an application specific integrated circuit (ASIC) or a microcontroller. The processor 110 may maintain a date and time as well as other functions (e.g., calculations or the like). The processor 110 may be operable to execute a control application 116 encoded in computer programming instructions stored in the storage 114 that enables the processor 110 to direct operation of the medicament delivery device 102. The control application 116 may be a single program, multiple programs, modules, libraries, or the like. The control application 116 may be responsible for implementing the control loop that provides feedback and adjustments to medicament dosages that are delivered to the user 108. The processor 110 also may execute computer programming instructions stored in the storage 114 for a user interface 117 that may include one or more display screens shown on display 109. The display 109 may display information to the user 108 and, in some instances, may receive input from the user 108, such as when the display 109 is a touchscreen.

The control application 116 may control delivery of a medicament to the user 108 per a control approach like that described herein. The storage 114 may hold histories 111 for the user 108, such as a history of basal deliveries, a history of bolus deliveries, and/or other histories, such as a meal event history, exercise event history, glucose level history, medicament delivery history, sensor data history and/or the like. These histories may be processed as will be described below to adjust basal medicament dosages to help reduce or eliminate persistent positive low level medicament excursions. The storage 114 also may include one or more basal profiles 115 that are used when the medicament delivery device is operating in open loop mode. In addition, the processor 110 may be operable to receive data or information. The storage 114 may include both primary memory and secondary memory. The storage 114 may include random access memory (RAM), read only memory (ROM), optical storage, magnetic storage, removable storage media, solid state storage or the like.

The medicament delivery device 102 may include one or more housings for housing its various components including a pump 113, a power source (not shown), and a reservoir 112 for storing a medicament for delivery to the user 108. A fluid path to the user 108 may be provided, and the medicament delivery device 102 may expel the medicament from the reservoir 112 to deliver the medicament to the user 108 using the pump 113 via the fluid path. The fluid path may, for example, include tubing coupling the medicament delivery device 102 to the user 108 (e.g., tubing coupling a cannula to the reservoir 112) and may include a conduit to a separate infusion site.

There may be one or more communications links with one or more devices physically separated from the medicament delivery device 102 including, for example, a management device 104 of the user 108 and/or a caregiver of the user 108, a sensor 106, a smartwatch 130, a fitness monitor 132 and/or another variety of wearable device 134. The communication links may include any wired or wireless communication links operating according to any known communications protocol or standard, such as Bluetooth®, Wi-Fi, a near-field communication standard, a cellular standard, or any other wireless protocol.

The medicament delivery device 102 may interface with a network 122 via a wired or wireless communications link. The network 122 may include a local area network (LAN), a wide area network (WAN) or a combination therein. A computing device 126 may be interfaced with the network, and the computing device may communicate with the medicament delivery device 102 or the management device 104.

The medicament delivery system 100 may include one or more sensor(s) 106 for sensing the levels of one or more analytes or for sensing environmental conditions. Examples of sensors 106 include a continuous glucose monitor, a heart rate monitor, a bloop pressure monitor, a temperature, sensor, a barometer, an accelerometer, etc. The sensor(s) 106 may be coupled to the user 108 by, for example, adhesive or the like and may provide information or data on one or more medical conditions and/or physical attributes of the user 108. The sensor(s) 106 may be physically separate from the medicament delivery device 102 or may be an integrated component thereof.

The medicament delivery system 100 may or may not also include management device 104. In some embodiments, no management device is not needed as the medicament delivery device 102 may manage itself. The management device 104 may be a special purpose device, such as a dedicated personal diabetes manager (PDM) device. The management device 104 may be a programmed general-purpose device, such as any portable electronic device including, for example, a dedicated controller, such as a processor, a micro-controller, or the like. The management device 104 may be used to program or adjust operation of the medicament delivery device 102 and/or the sensors 106. The management device 104 may be any portable electronic device including, for example, a dedicated device, a smartphone, a smartwatch or a tablet. In the depicted example, the management device 104 may include a processor 119 and a storage 118. The processor 119 may execute processes to manage a user's glucose levels and to control the delivery of the medicament to the user 108. The medicament delivery device 102 may provide data from the sensors 106 and other data to the management device 104. The data may be stored in the storage 118. The processor 119 may also be operable to execute programming code stored in the storage 118. For example, the storage 118 may be operable to store one or more control applications 120 for execution by the processor 119. The one or more control applications 120 may be responsible for controlling the medicament delivery device 102, such as by controlling the AID delivery of insulin to the user 108. The storage 118 may store the one or more control applications 120, histories 121 like those described above for the medicament delivery device 102, one or more basal profiles 135 and other data and/or programs.

A display 127, such as a touchscreen, may be provided for displaying information. The display 127 may display user interface (UI) 123. The display 127 also may be used to receive input, such as when it is a touchscreen. The management device 104 may further include input elements 125, such as a keyboard, button, knobs, or the like, for receiving input form the user 108.

The management device 104 may interface with a network 124, such as a LAN or WAN or combination of such networks via wired or wireless communication links. The management device 104 may communicate over network 124 with one or more servers or cloud services 128. Data, such as sensor values, may be sent, in some embodiments, for storage and processing from the medicament delivery device 102 directly to the cloud services/server(s) 128 or instead from the management device 104 to the cloud services/server(s) 128. The cloud services/server(s) 128 may provide output from the model 115 as needed to the management device 104 and/or medicament delivery device 102 during operation.

Other devices, like smartwatch 130, fitness monitor 132 and wearable device 134 may be part of the medicament delivery system 100. These devices 130, 132 and 134 may communicate with the medicament delivery device 102 and/or management device 104 to receive information and/or issue commands to the medicament delivery device 102. These devices 130, 132 and 134 may execute computer programming instructions to perform some of the control functions otherwise performed by processor 110 or processor 119, such as via control applications 116 and 120. These devices 130, 132 and 134 may include displays for displaying information. The displays may show a user interface for providing input by the user 108, such as to request a change or pause in dosage or to request, initiate, or confirm delivery of a bolus of a medicament, or for displaying output, such as a change in dosage (e.g., of a basal delivery amount) as determined by processor 110 or management device 104. These devices 130, 132 and 134 may also have wireless communication connections with the sensor 106 to directly receive analyte measurement data.

A wide variety of medicaments may be delivered by the medicament delivery device 102. The medicament may be insulin for treating diabetes. The medicament may be glucagon for raising a user's glucose level. The medicament may also be a glucagon-like peptide (GLP)-1 receptor agonists for lowering glucose or slowing gastric emptying, thereby delaying spikes in glucose after a meal. Alternatively, the medicament delivered by the medicament delivery device 102 may be one of a pain relief agent, a chemotherapy agent, an antibiotic, a blood thinning agent, a hormone, a blood pressure lowering agent, an antidepressant, an antipsychotic, a statin, an anticoagulant, an anticonvulsant, an antihistamine, an anti-inflammatory, a steroid, an immunosuppressive agent, an antianxiety agent, an antiviral agents, a nutritional supplement or a vitamin.

The functionality described below for the exemplary embodiments may be under the control of or performed by the control application 116 of the medicament delivery device 102 or the control application 120 of the management device 104. In some embodiments, the functionality may be under the control of or performed by the cloud services or servers 128, the computing device 126 or by the other enumerated devices, including smartwatch 130, fitness monitor 132 or another wearable device 134.

The medicament delivery device 102 may operate in an open loop mode and in a closed loop mode. In the open loop mode, the user 108 manually inputs the amount of medicament to be delivered (such as per hour) for segments of the day. The inputs may be stored in a basal profile 115, 135 for the user 108. In other embodiments, a basal profile may not be used. The control application 116, 120 uses the input information from the basal profile 115, 135 to control basal medicament deliveries in open loop mode. In contrast, in the closed loop mode, the control application 116, 120 determines the medicant delivery amount for the user 108 on an ongoing basis based on a feedback loop. For an insulin delivery device, the aim of the closed loop mode is to have the user's glucose level at a target glucose level. The basal dosages may be delivered at fixed regular intervals, designated as cycles, such as every five minutes.

In the exemplary embodiments, the functionality described below may be realized by executing the control application 116 or 120 or by running a control application on other devices, such as smartwatch 130, fitness monitor 132 or other type of wearable device 134. More generally, the functionality may be realized by computer programming instructions executing on a processor for controlling the medicament delivery device 102.

As discussed above, the user 108 may have the option of setting the medicament delivery device 102 into a flight mode. The flight mode adjusts the settings of the medicament delivery device 102 to adapt to the altered environmental conditions, such as a reduced ambient air pressure, found in the cabin of the plane during flight.

Figure 2A:
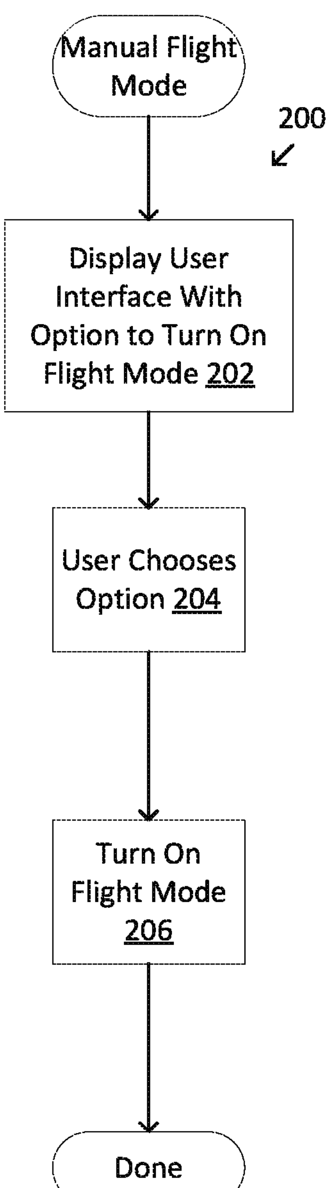
FIG. 2A depicts a flowchart of illustrative steps that may be performed in exemplary embodiments to facilitate manual selection of flight mode.

The initiation of flight mode may be performed manually. FIG. 2A depicts a flowchart 200 of illustrative steps that may be performed in exemplary embodiments to manually initiate flight mode. At 202, a user interface with an option to turn on flight mode may be displayed. For example, such a user interface may be displayed on the display 109 of the medicament delivery device 102 or the display 127 of the management device 104. Still further, the user interface may be displayed in some exemplary embodiments on other devices, such as smartwatch 130, fitness monitor 132 or another type of wearable device 134.

Figure 2B:
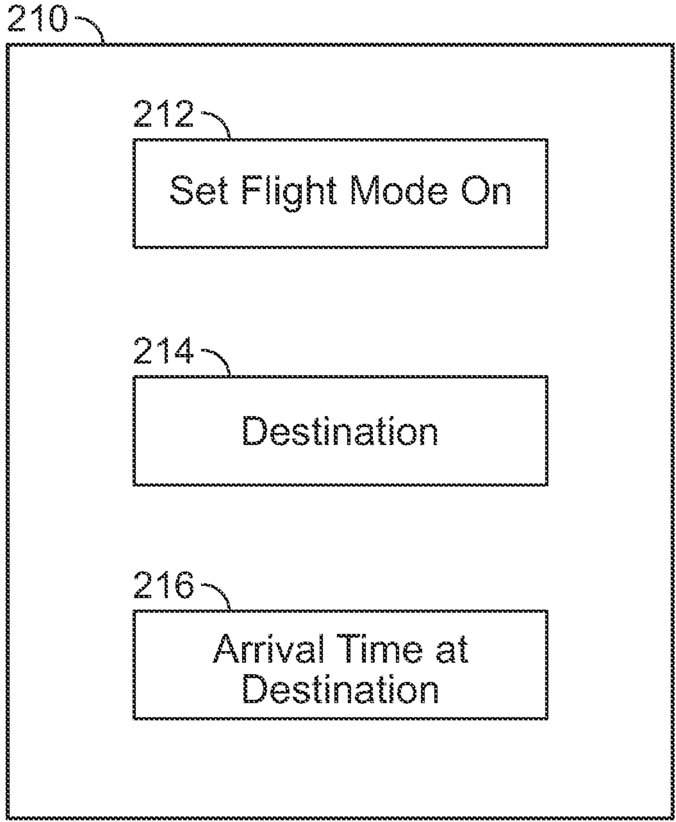
FIG. 2B depicts an illustrative user interface for a user to manually select flight mode.

FIG. 2B depicts an illustrative user interface 210 that may be displayed on the display 127 of the management device 104 to facilitate the transition to flight mode. The user interface 210 may, in some exemplary embodiments, instead be displayed on display 109 of the medicament delivery device 102 or on other devices. The user interface 210 may be always accessible by the user 108 or may appear automatically only when it is determined that the user 108 is likely on a flight, as will be discussed below. The user interface 210 may include a user interface element 212, such as a button or other variety of selectable element, for turning on the flight mode. The user interface 210 may also include a destination element 214, for specifying the destination of the flight. Selection of the destination element 214 may cause a dropdown list of destinations to be displayed, and the user 108 may select one of the destinations. The user interface 210 may further include element 216 that may be selected to enter the arrival time at the destination. Selection of element 216 may cause a text box that enables entry of the arrival time to be displayed. This information enables the medicament delivery device 102 to know the duration of the flight and when flight mode should be turned off. Alternative user interfaces may also include user interface elements for specifying scheduled arrival time at a destination, duration of the flight and/or name of destination. Those skilled in the art will appreciate other varieties of user interfaces may be used to manually turn on flight mode. The user interface need not include the destination element 214 or the arrival time element. Moreover, the user interface may include user interface elements, such as menus, radio buttons, switches, etc.

With reference to FIG. 2A, at 204, the user 108 may choose the Set Flight Mode On option 212 in the user interface 210. The flight mode may then be turned on until switched back to normal mode or to cool down mode, as will be discussed below.

Figure 3A:
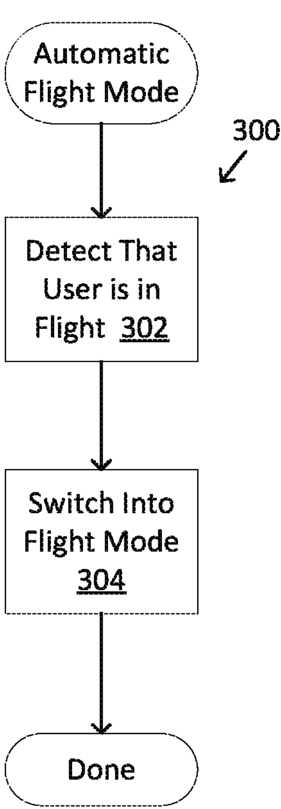
FIG. 3A depicts a flowchart of illustrative steps that may be performed in exemplary embodiments to automatically switch to flight mode responsive to data.

Another option is for the medicament delivery device 102 to be automatically switched into flight mode rather than by manual switching to flight mode. FIG. 3A depicts a flowchart 300 of illustrative steps that may be performed in exemplary embodiments to automatically switch to flight mode. At 302, the management device 104, the medicament delivery device 102 or other enumerated devices 130, 132 or 134 may automatically detect when the user 108 is in flight on a plane. Responsive to detecting that the user 108 is in flight, at 304, the medicament delivery device 102 may be switched into flight mode.

Figure 3B:
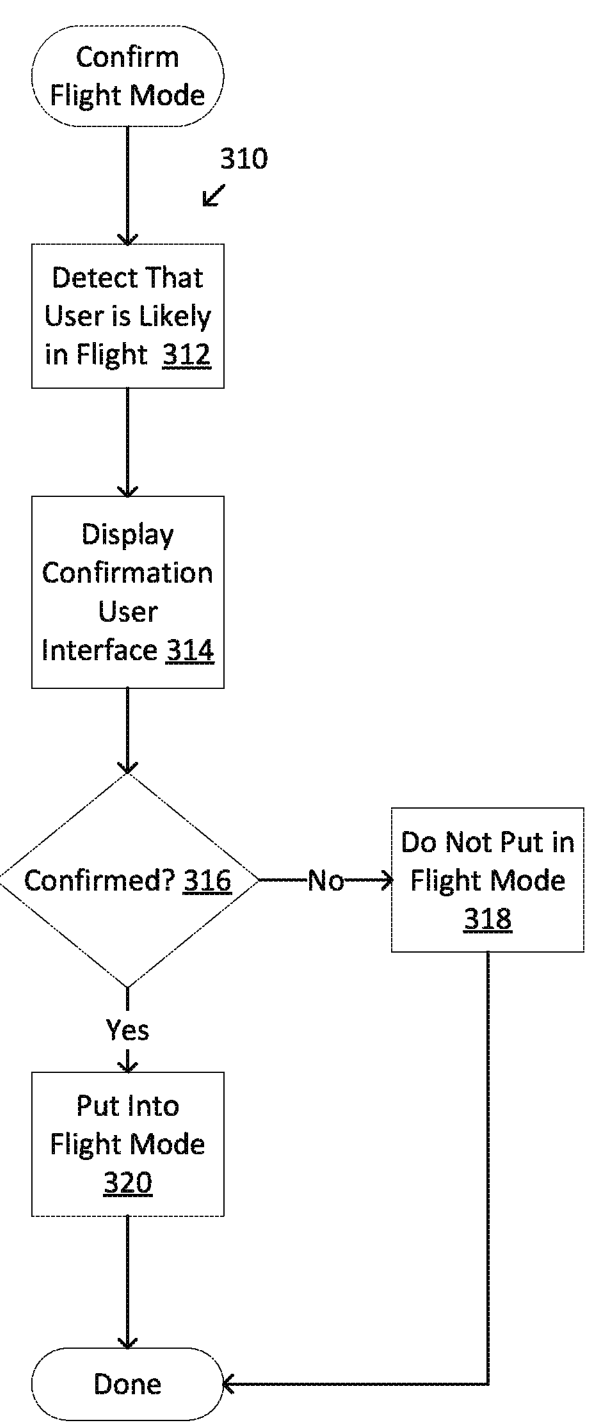
FIG. 3B depicts a flowchart of illustrative steps that may be performed in exemplary embodiments to switch to flight mode after user confirmation.

Another option is for the switchover to flight mode to not take place automatically but rather to require confirmation first. FIG. 3B depicts a flowchart 310 of illustrative steps that may be performed in exemplary embodiments in such an instance. At 312, it is detected that the user 108 likely is in flight as will be detailed below. At 314, a confirmation user interface may be displayed in response to the automatic detection that the user 108 likely is in flight. The confirmation user interface may contain a button or other user interface element for confirming the switch to flight mode and/or an element for not confirming the transition to flight mode. The user interface, for example, may contain a user interface element like 212, as described above. At 316, a check is made whether the user 108 has confirmed the transition to flight mode based on activity or inactivity relative to the confirmation user interface. If confirmed, at 320, the medicament delivery device 102 is put into flight mode. If not confirmed, at 318, the medicament delivery device is not put into flight mode.

Figure 4:
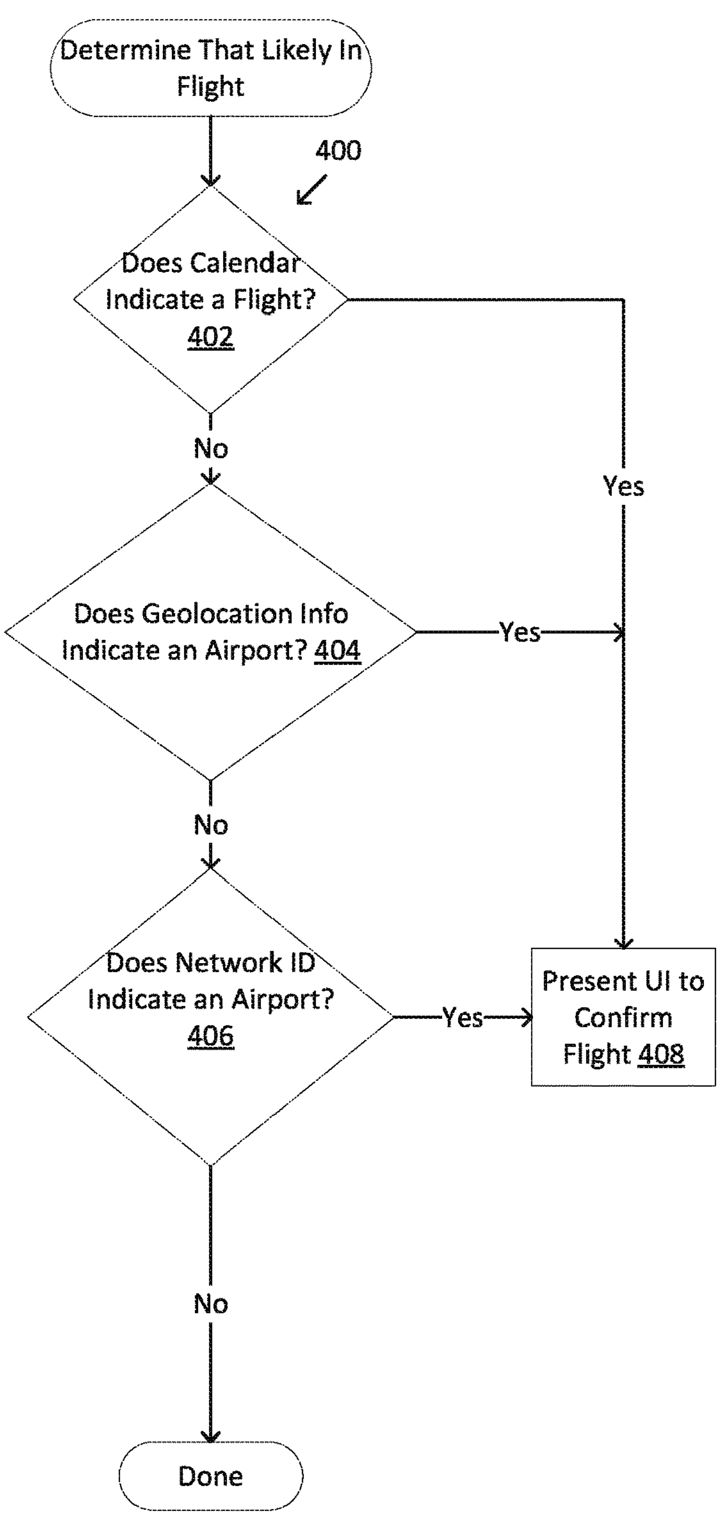
FIG. 4 depicts a flowchart of illustrative steps that may be performed in exemplary embodiments to determine that a user is in flight.

FIG. 4 depicts a flowchart 400 of illustrative steps that may be performed in exemplary embodiments in determining that the user 108 is likely in flight or will be soon (see 312 in FIG. 3B). At 402, a user calendar, such as on management device 104, is accessed to see if the calendar shows a flight for the current day and time. If so, at 408, a confirmation user interface is presented to the user 108 to confirm the flight. If not, at 404, a check is made whether geolocation information indicates that the user 108 is at an airport. If the user 108 is at the airport, it may be that the user 108 is preparing to take a flight. The geolocation information may be Global Positioning System (GPS) data, for example. Most cellular phones have GPS capability; hence, the management device 104 may have such a capability. If the geolocation information indicates that the user 108 is at the airport or at a particular gate at the airport, at 408 the confirmation user interface is presented to the user 108 when the flight is scheduled to be in flight. The flight time may be obtained as part of the user interface. If not, at 406, a check is made whether the network ID of a WiFi network to which the medicament delivery device 102 and/or the management device 104 is connected is that of a network for an airport. If so, the confirmation user interface is presented to the user 108 when the flight is scheduled to be in flight. If not, no further action is taken to obtain a confirmation.

It should be appreciated that the depicted steps of FIG. 4 are intended to be illustrative but not limiting. Not all of the steps need to be performed in some exemplary embodiments, and other steps may be substituted for those shown. The steps look for indicia that the user 108 is at the airport and/or scheduled to fly. The indicia may not be reliable enough to rely upon them alone. Hence, the confirmation may be warranted.

Figure 5A:
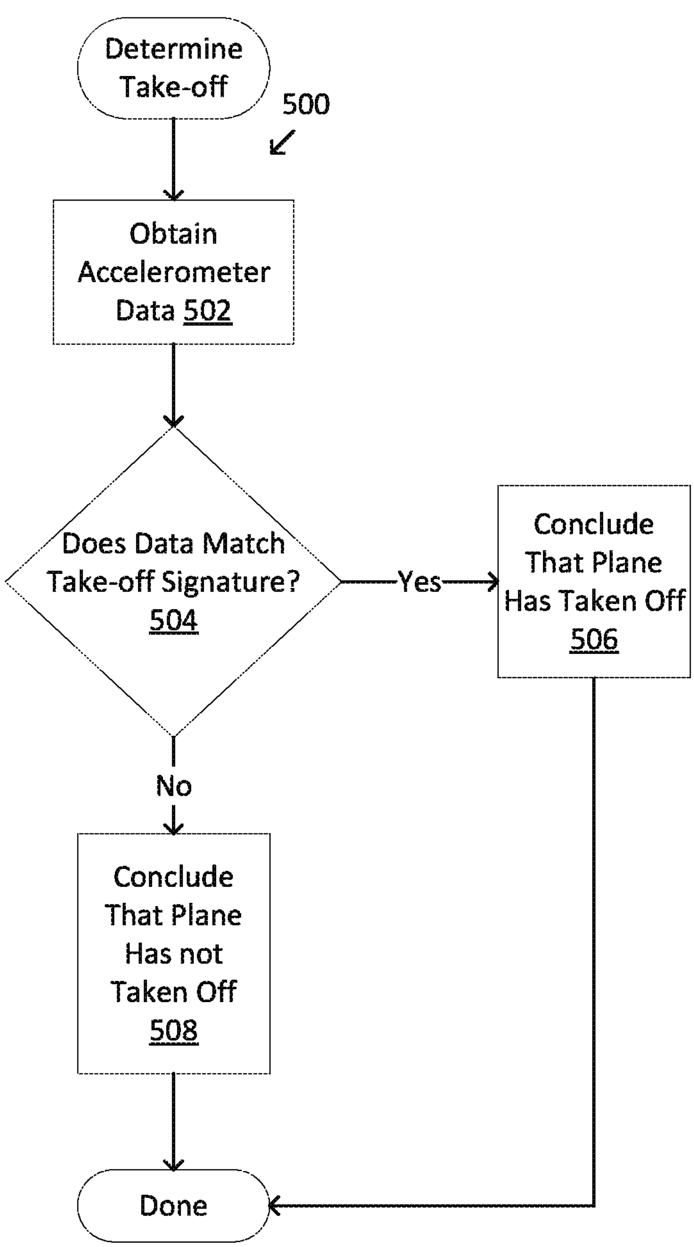
FIG. 5A depicts a flowchart of illustrative steps that may be performed in exemplary embodiments to determine that a plane carrying a user has taken off.

Some indicia may be more reliable of indicating that a user 108 is on a plane and in flight. For instance, accelerometer data may be reliable in this regard. Thus, for automatic switching to flight mode (see FIG. 3A), accelerometer data may be used. FIG. 5A depicts a flowchart 500 of illustrative steps that may be performed in exemplary embodiments to determine whether the user 108 is on a plane that has taken off and hence in flight. At 502, accelerometer data is obtained from an accelerometer in the medicament delivery device 102 or the management device 104. At 504, a comparison between the obtained accelerometer data and a takeoff accelerometer signature is performed. If there is a match between the obtained accelerometer data and the takeoff accelerometer signature, it is concluded that the plane has taken off at 506. In contrast, at 508, if there is no match between the obtained accelerometer data and the takeoff accelerometer signature, it is concluded that the plane has not taken off.

Figure 5B:
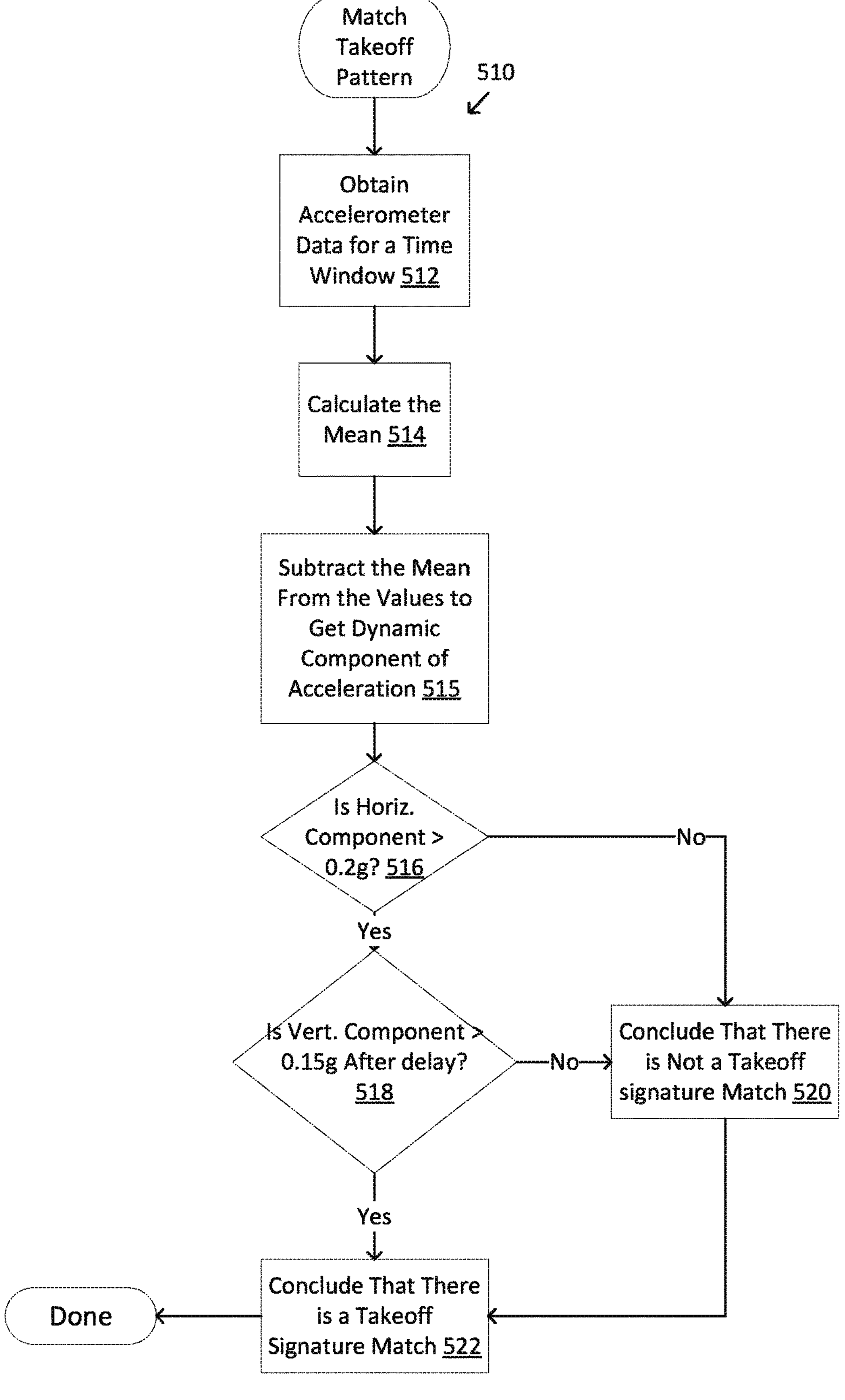
FIG. 5B depicts a flowchart of illustrative steps that may be performed in exemplary embodiments to match accelerometer data with a takeoff accelerometer signature.

FIG. 5B depicts a flowchart 510 of illustrative steps that may be performed in exemplary embodiments in matching the obtained accelerometer data to the takeoff accelerometer signature. At 512, accelerometer data is obtained for a time window, such as a period of typical of a takeoff sequence once acceleration begins. At 514, a mean value is calculated from the obtained accelerometer data. Calculating of the mean entails summing each piece of accelerometer data in the time window and dividing the sum by the number of accelerometer data values in the window. At 515, the mean is subtracted from each of the accelerometer data values in the time window to obtain the dynamic component of acceleration. The dynamic component of acceleration has a horizontal component and a vertical component. At 516, a check is made whether the magnitude of the horizontal component of acceleration during the time window exceeds 0.2 g. During typical takeoffs, accelerations are about 0.4 g in the horizontal direction. Hence, the check at 516 is looking for such horizontal component of acceleration values. At 520, if there are no horizontal components of acceleration that exceed 0.2 g, it is concluded that there is not a takeoff accelerometer signature match. On the other hand, at 518, if there is a horizontal component of acceleration with a magnitude that exceeds 0.2 g, a check is made whether it is a vertical component of acceleration that is greater than 0.2 g after a 20 second delay from when the horizontal component of acceleration began to exceed 0.2 g. The delay is provided to account for the period where the plane is accelerating along the runway before the plane lifts off the ground. The vertical component of acceleration will appear when the plane has lifted off the ground. Typically, this vertical component of acceleration may reach 1.25 g (0.25 g above baseline). At 520, if the vertical component of acceleration does not exceed 0.2 g after the delay, it is concluded that there is not a takeoff accelerometer signature match. However, at 522, if the vertical part of acceleration exceeds 0.2 g, it is concluded that there is a takeoff accelerometer signature match.

Flight mode may entail changes in the medicament delivery device 102 relative to normal operation. Among the changes may be a change in delivery of basal medicament deliveries. Basal medicament deliveries typically are small dosages of medicament delivered at regular intervals. For example, where the medicament is insulin, the medicament delivery device 102 may deliver small basal doses of insulin to the user 108 per cycle, where a cycle is, for instance, a 5-minute period. The basal doses of insulin seek to control the glucose level of the user 108 on an ongoing basis to keep the glucose level in an acceptable range around a target glucose level.

Figure 6:
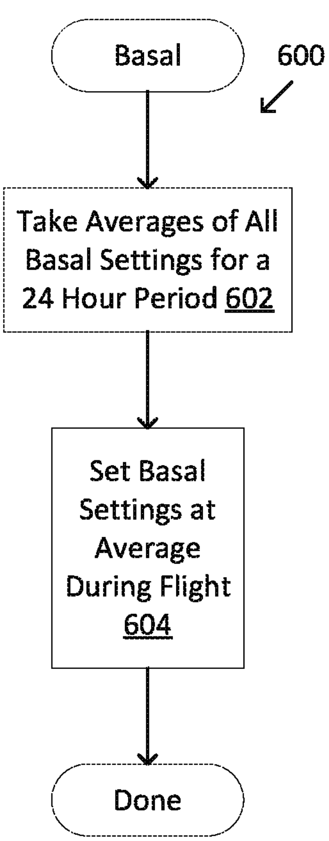
FIG. 6 depicts a flowchart of illustrative steps that may be performed in exemplary embodiments to adjust basal settings.

FIG. 6 depicts a flowchart of illustrative steps that may be performed in exemplary embodiments to adjust basal medicament deliveries in flight mode. Conventionally, a user 108 of a medicament delivery device 102 may have basal delivery settings that are optimized for periods of the day, such as morning, afternoon, evening and overnight. Travelling long distances by plane may entail passing through multiple time zones. Thus, it may be confusing as to what settings to apply. Hence, it appears to be better to apply a uniform setting while the user 108 is in flight. FIG. 6 depicts a flowchart 600 of illustrative steps that may be performed to determine and apply such uniform settings. At 602, the averages of the basal settings for a 24-hour period are averaged. At 604, the averages of the basal settings are used as the basal settings for the flight.

Figure 7:
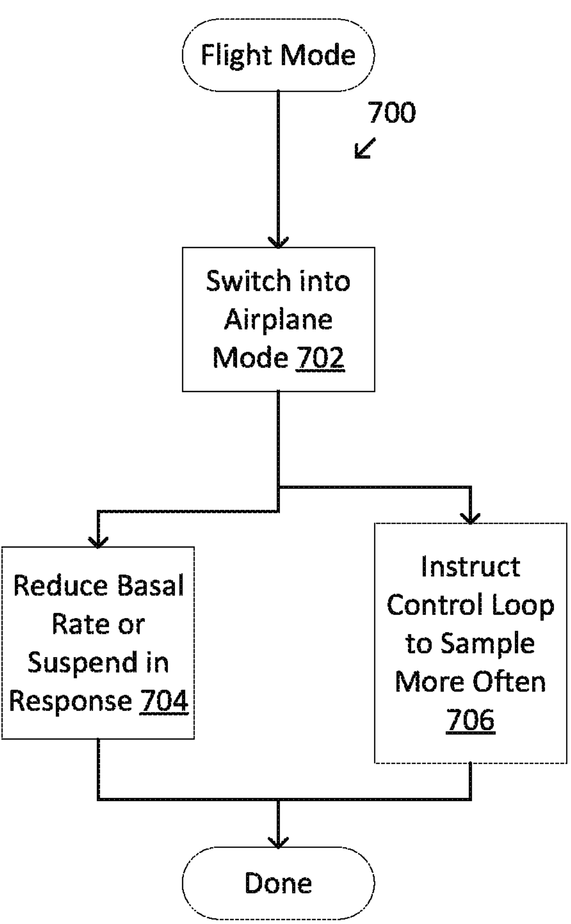
FIG. 7 depicts a flowchart of illustrative steps that may be performed in exemplary embodiments to adjust medicament delivery responsive to a change to flight mode.

Other changes to the basal medicament deliveries alternatively may be made when entering flight mode. FIG. 7 depicts a flowchart 700 of illustrative steps that may be performed in exemplary embodiments. At 702, the medicament delivery device 102 is switched into flight mode. Then, either 704 or 706 may be performed. At 704, the basal delivery rate is reduced or suspended. This reduction or suspension is responsive to the reduced ambient air pressure in the plane during flight. As a result, there is an increased risk of over-delivery of medicament. In the case where the medicament is insulin, the over delivery may result in hypoglycemia. By reducing or suspending the delivery of the medicament, this approach reduces the risk of over delivery of the medicament. At 706, as another option the control loop may sample more often to ensure that the medicament delivery device 102 responds quickly to any over delivery. In the case where the medicament is insulin, the sampling obtains glucose values for the user 108 from a sensor 106, such as a CGM. By sampling more quickly, the control loop may respond to a drop in glucose for the user 108 before the drop gets too significant. In contrast with a convention insulin delivery device the cycle length of 5 minutes may be too long such that a user's glucose level may change a great deal between readings, and hence, the control loop may be late to respond to the change.

Figure 8A:
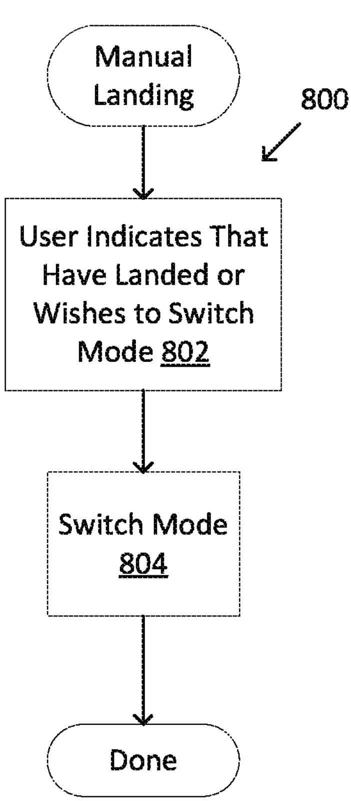
FIG. 8A depicts a flowchart of illustrative steps that may be performed in exemplary embodiments to switch modes responsive to a manual indication that the plane has landed.

The mode of operation of the medicament delivery device 102 may be changed upon landing of a flight carrying the user 108. There may be a number of different ways of determining whether a flight has landed. In a first way, as depicted in the flowchart 800 of FIG. 8A, the determination of whether the flight has landed is made by the user 108. At 802, the user 108 indicates that the plane has landed or indicates that the user 108 wishes to switch the mode of operation of the medicament delivery device 102. For example, there may be a user interface element on the management device 104 that may be activated by the user 108 to indicate that the plane has landed. There also may be a user interface element on the management device 104 that enables user 108 to manually switch the mode of operation of the medicament delivery device 102. Upon the user 108 indicating that the plane has landed or upon the user 108 indicating that the user 108 wishes to switch modes, at 804, the mode of operation of the medicament delivery device 102 is changed. As will be discussed in more detail below, the mode may be changed back to the normal mode of operation or may be switched to a cool off mode, which will be discussed in more detail below. In other exemplary embodiments, the mode may be switched to different varieties of modes of operation.

Figure 8B:
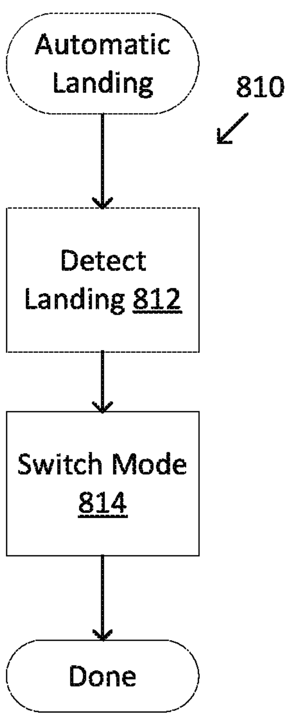
FIG. 8B depicts a flowchart of illustrative steps that may be performed in exemplary embodiments to automatically detect landing of a plane carrying the user and switch out of flight mode in response to the landing.

The detection of the landing of the airplane carrying the user 108 need not be performed manually; rather, in some exemplary embodiments, the detection the landing may be performed automatically by the control application 118, 120 based on data that is available to the management device 104 or the medicament delivery device 102. FIG. 8B depicts a flowchart 810 of illustrative steps that may be performed in exemplary embodiments to automatically detect landing and automatically switch modes. At 812, the control application 118, 120 detects that the plane has landed. As will be detailed below, the detection may be, for example, based upon accelerometer data. Upon detecting that the plane has landed, at 814, the mode of operation of the medicament delivery device 102 may be switched.

Figure 9A:
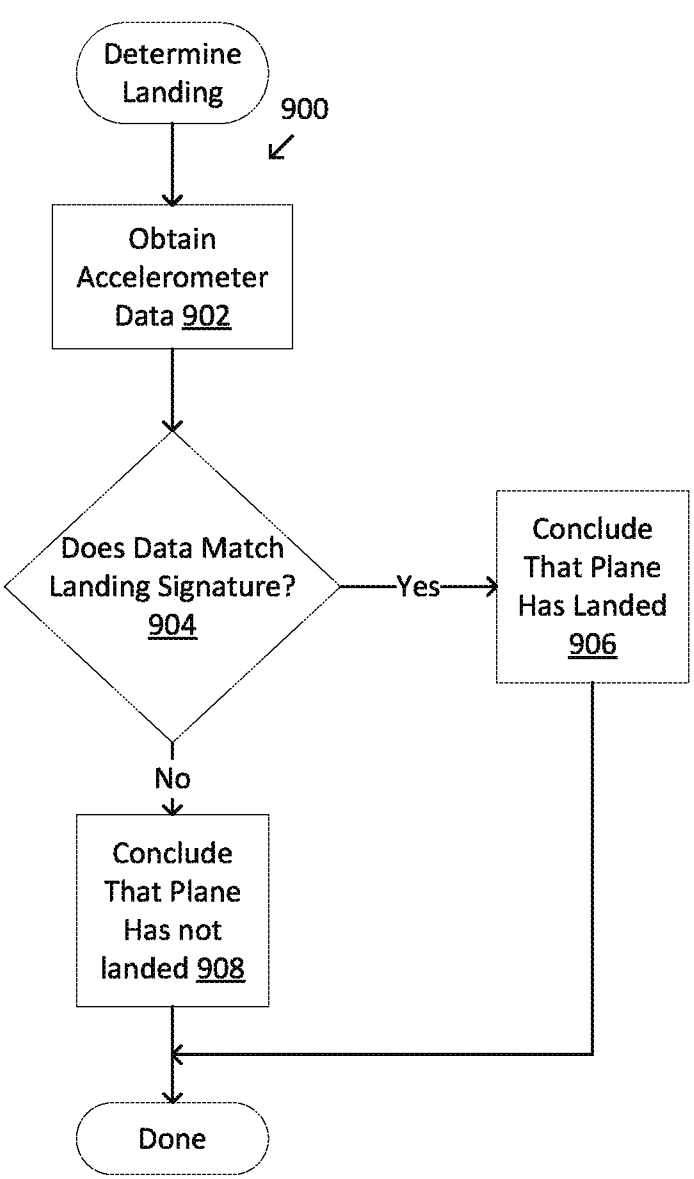
FIG. 9A depicts a flowchart of illustrative steps that may be performed in exemplary embodiments to automatically determine that the plane carrying the user has landed based on accelerometer data.

As was mentioned above, the landing of the plane carrying the user 108 may automatically be determined based upon accelerometer data. FIG. 9A depicts a flowchart 900 of illustrative steps that may be performed in exemplary embodiments to determine whether a plane has landed based upon the accelerometer data. At 902, the accelerometer data is obtained for a time window. The time window is sufficiently long to capture the time it takes for a plane to touchdown and then decelerate to a taxiing speed. At 904 a comparison is performed to determine if the accelerometer data that has been obtained matches the accelerometer data that is typical of a plane landing (i.e., a landing accelerometer signature). If the data matches the landing accelerometer signature, it is concluded that the plane has landed at 906. If, in contrast, is concluded that the accelerometer data does not match landing accelerometer signature, is concluded that the plane is not landed at 908. This use of the accelerometer data enables automatic detection of a plane landing by a programmatic mechanism, like the control application 116, 120.

Figure 9B:
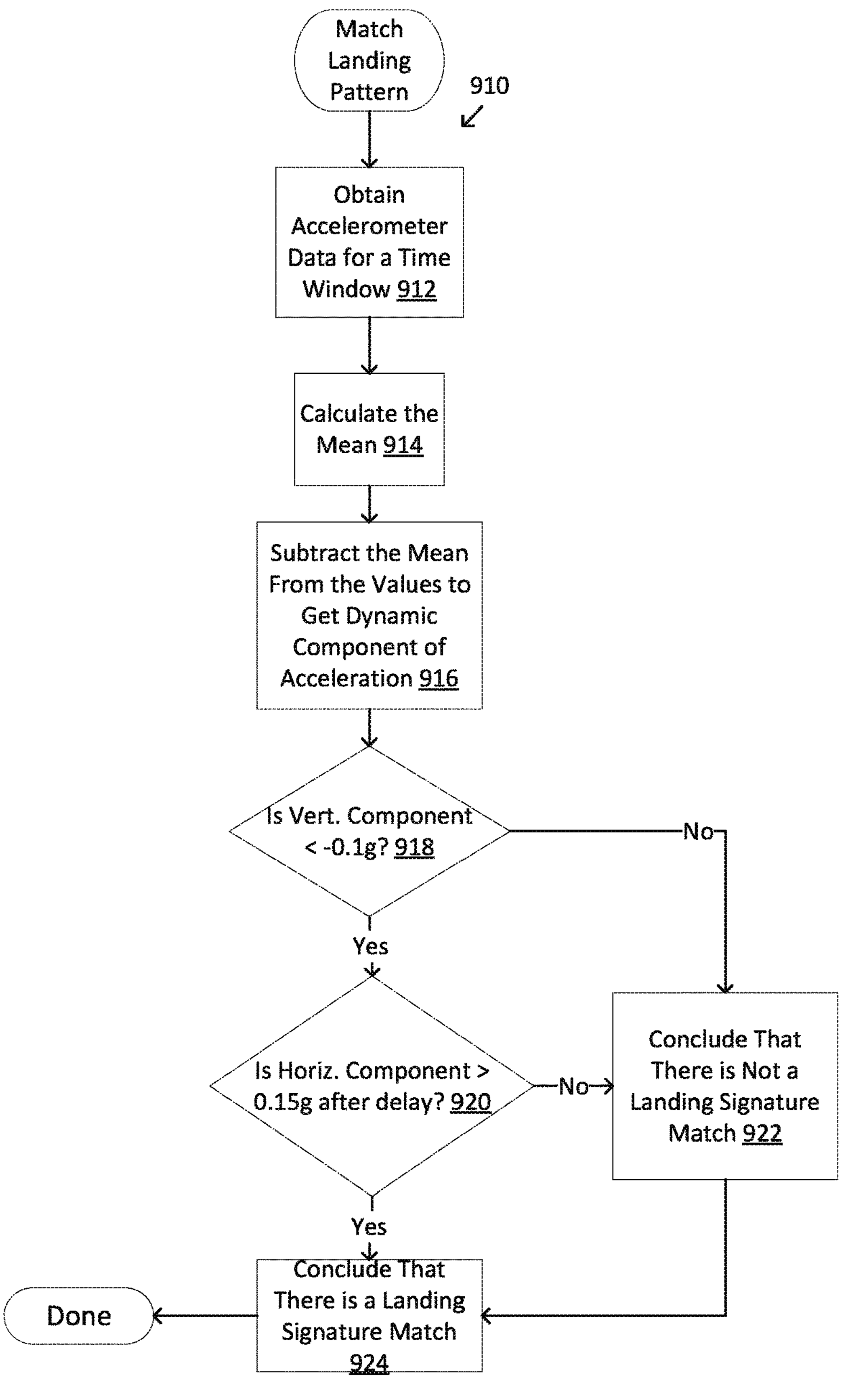
FIG. 9B depicts a flowchart of illustrative steps that may be performed in exemplary embodiments to match accelerometer data with a landing accelerometer signature.

FIG. 9B depicts a flowchart 910 of illustrative steps that may be performed in exemplary embodiments to match the obtained accelerometer data to the landing accelerometer signature. At 912, the accelerometer data for a time window is obtained as has been described above. The mean value of the acceleration data values obtained from the accelerometer is calculated at 914. The calculation of the mean may entail summing the accelerometer data values within the time window and dividing by the number of values. At 916, the mean is subtracted from each of the values in the time window to obtain a dynamic component of acceleration for each value at 916. When a flight is making a descent, the downward gravitational forces typically in the range of 0.75 g (0.25 g below baseline). At touchdown, there is an upward impulse with the matching upward acceleration. The runway braking forces are typically the magnitude of 0.25 g. At 918, a check is made whether the vertical component of the dynamic component of acceleration is less than −0.1 g. If not, at 922, it is concluded that there is not a landing pattern match with the landing accelerometer signature. If the vertical component of the dynamic component acceleration is less than −0.1 g, a check is made whether the horizontal component of the dynamic component of acceleration is greater than 0.15 g after a delay at 920. The delay represents the time before the plane touches down after the descent. If the plane is braking, the horizontal component of the dynamic component of acceleration should be greater than 0.15 g (in magnitude). Hence, if that is the case, it is concluded that there is a landing accelerometer signature match at 924. If that is not the case, it is concluded that there is not a landing accelerometer signature match at 922.

Figure 10:
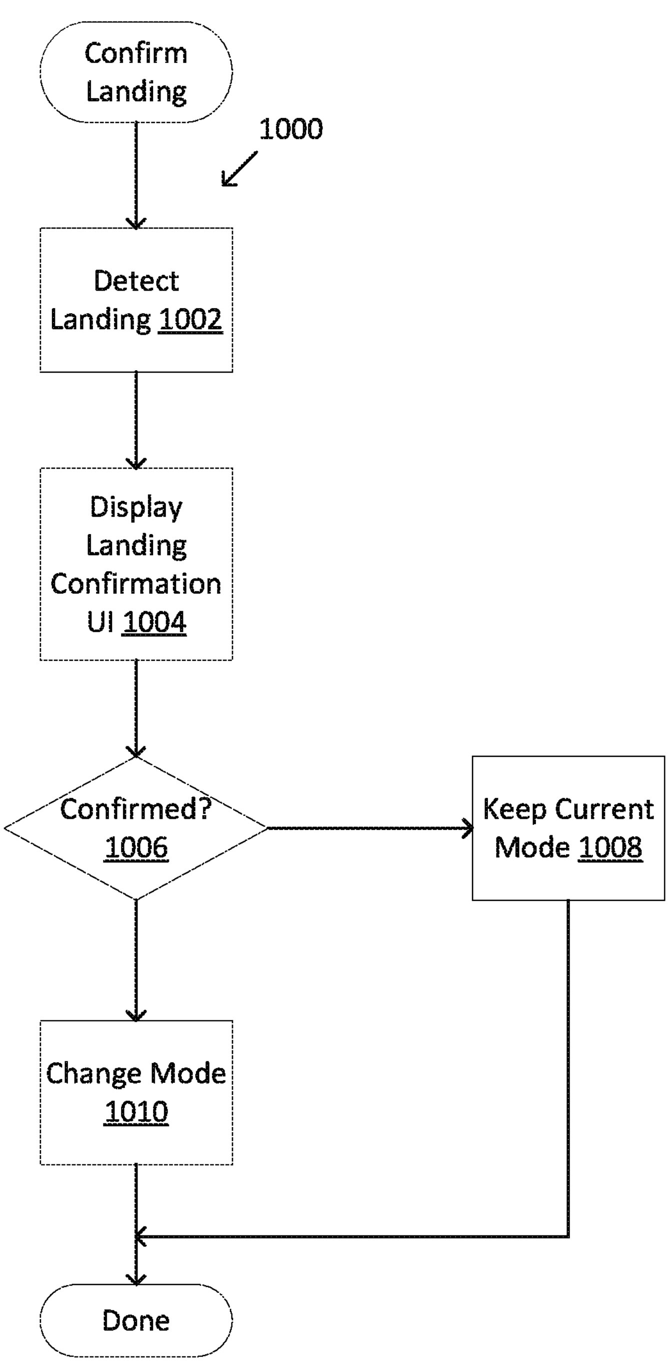
FIG. 10 depicts a flowchart of illustrative steps that may be performed in exemplary embodiments to change out of flight mode responsive to a confirmation of landing by the user.

In other exemplary embodiments, a combination of automatic detection of landing and user confirmation may be used. FIG. 10 depicts a flowchart 1000 of illustrative steps that may be performed in exemplary embodiments to detect and confirm landing of the plane carrying the user 108. At 1002, the landing is detected. This may be the result of processing accelerometer data or other data indicative of the landing. At 1000, a landing confirmation user interface is displayed on the management device 104. The landing confirmation user interface contains one or more elements that enable the user 108 to confirm that the plane has landed or to indicate that the plane has not landed. At 1006, a determination is made whether the user 108 has confirmed landing or not. At 1008, if landing is not confirmed, the current mode of operation of the medicament delivery device 102 is maintained. However, if the user 108 has confirmed landing, at 1010, the mode of operation of the medicament delivery device 102 is changed.

Figure 11:
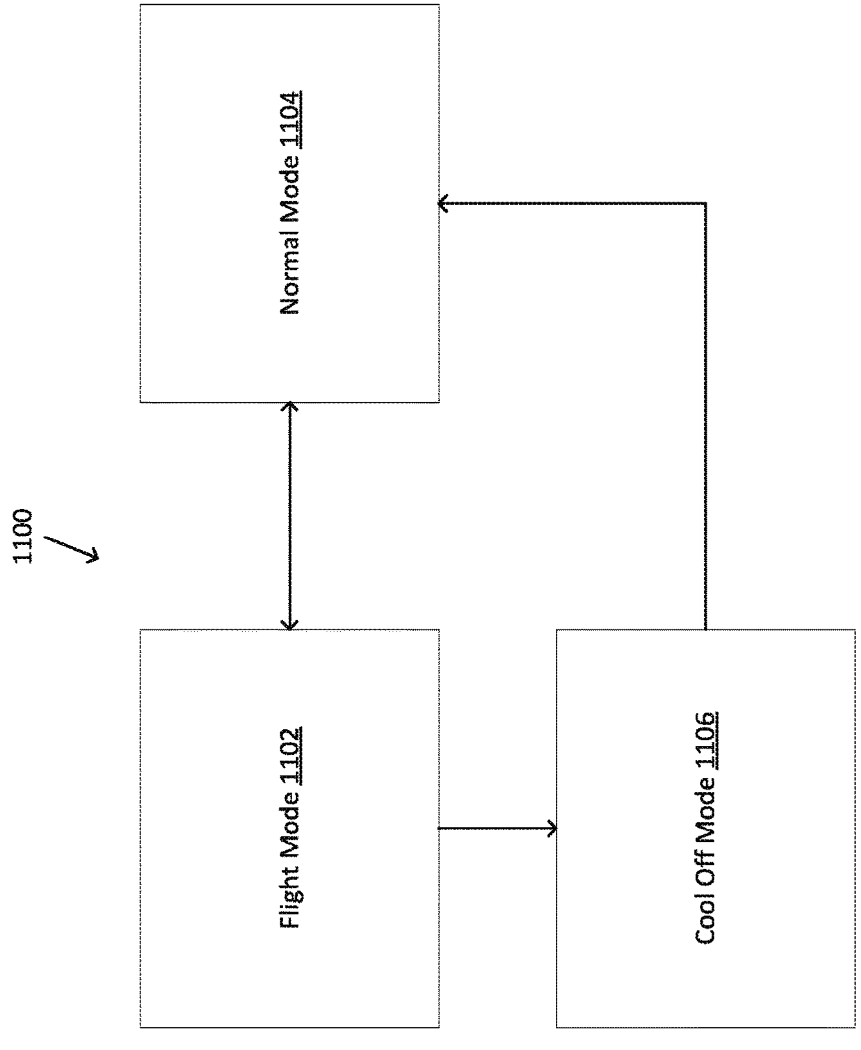
FIG. 11 depicts transitions between modes of the medicament delivery device in exemplary embodiments.
Figure 12:
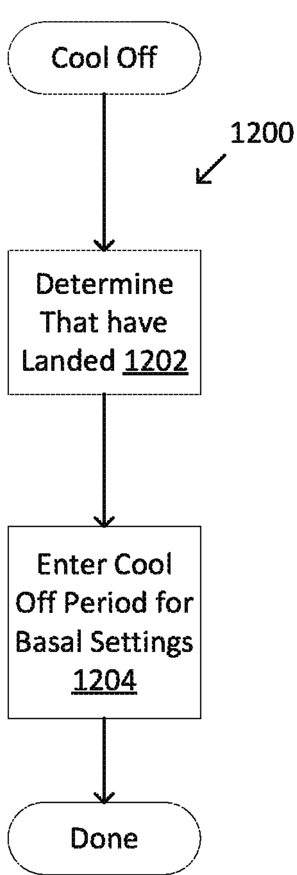
FIG. 12 depicts a flowchart of illustrative steps that may be performed in exemplary embodiments to enter cool off mode.

FIG. 11 depicts a block diagram 1100 that illustrates the switching of modes upon landing. While in flight, the medicament delivery device 102 operates in a flight mode 1102, as has been described above. Upon landing, the mode may be switched back to the normal mode 1104 of the medicament delivery device 102. Thus, the mode of operation of the medicament delivery device 102 may toggle from normal mode before getting on the plane to flight mode 1102 while on the plane and in flight and then back to normal mode 1104. Alternatively, if the flight is sufficiently long so as to travel through multiple time zones, the transition may be from flight mode 1102 to cool off mode 1106 upon landing. The cool off mode seeks to provide a transition after traveling large distances across multiple time zones. The cool off mode seeks to provide the user 108 with time to acclimatize to the new time zone at the flight destination. Thus, as shown in the flowchart 1200 of FIG. 12, a determination may be made that the plane carrying the user 108 has landed at 1202, and at 1204, the mode of operation of the medicament delivery device is changed to cool off mode. The aim of the cool off mode is to give the user 108 time to adjust the new time zone by transitioning settings from the flight mode back to a normal mode for the new time zone. A suitable length for the cool off period may be three days. Thus, the transition from the cool off mode 1106 may be to the normal mode 1104 as shown in FIG. 11.

Exemplary embodiments may also prevent delivery of boluses of medicaments during non-ideal environmental conditions that are encountered in a flight. Specifically, there are periods in a flight when it is not desirable for a bolus of medicament to be delivered. For instance, there are periods of low ambient air pressure where delivery of a medicament bolus may result in over-delivery of the medicament to the user 108. It also may not be desirable to deliver a medicament bolus when the user 108 is experiencing excessive acceleration or deceleration. Excessive acceleration during takeoff or banked turns may result in decreased ambient air pressure and hence, possible over-delivery of medicament. Excessive deceleration during landing may result in heightened air pressure. The heightened air pressure may result in under-delivery of a medicament. As mentioned above, there may also be flow anomalies, effects of mechanical vibrations from high accelerations or decelerations and physiological responses to acceleration/decelerations that make it undesirable to deliver a bolus of medicament when such non-ideal environmental conditions are present.

Figure 13:
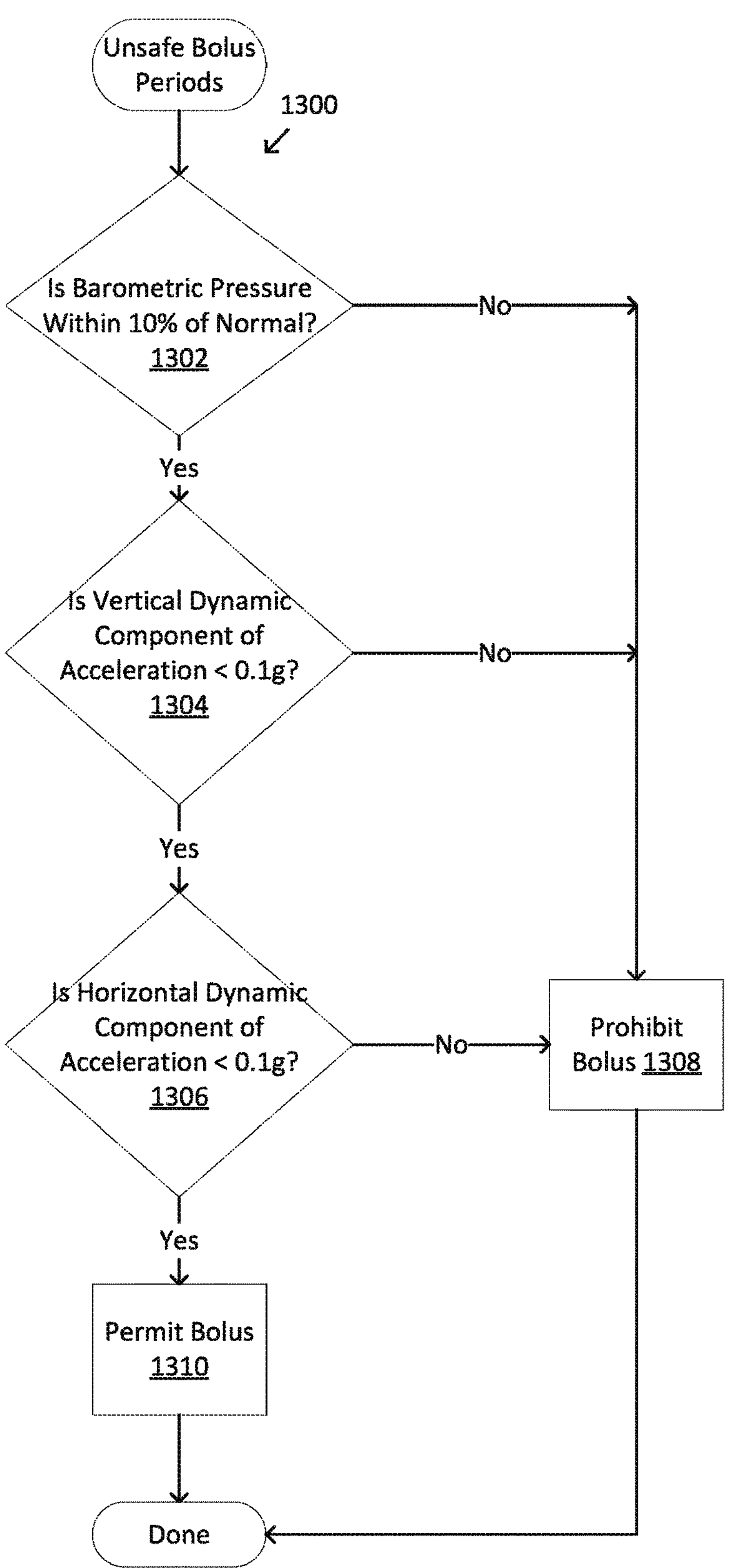
FIG. 13 depicts a flowchart of illustrative steps that may be performed in exemplary embodiments to detect non-ideal environmental conditions and prevent delivery of medicament boluses to the user during non-ideal environmental conditions.

The exemplary embodiments may automatically detect such non-ideal environmental conditions and prevent bolus medicament delivery during such conditions. FIG. 13 depicts a flowchart 1300 of illustrative steps that may be performed in exemplary embodiments to detect and respond to such non-ideal environmental conditions. At 1302, barometric pressure may be checked to see if the barometric pressure is within 10% of normal. A barometric sensor may be included among the sensor(s) 106 in the medicament delivery device 102 or the management device 104. However, such barometric sensors may be expensive and may not be found in the medicament delivery device 102 or the management device. As such, the barometric pressure may be obtained from a data source, such as a weather website that is accessible to the medicament delivery device 102 or the management device 104. In such instances, at 1308, the delivery of a medicament bolus is prohibited until the non-ideal environmental conditions no longer persist. Another type of environmental condition that can be checked is the magnitude (i.e., absolute value) of the vertical dynamic component of acceleration, which as previously described may be indicative of landing or taking off. Accordingly, at 1304, a check is made whether the absolute value of the vertical dynamic component of acceleration is less than 0.1 g. If not, it indicates that the plane is not likely in a cruising portion of a flight but rather likely is taking off or landing. In such instances, delivery of a medicament bolus is prohibited at 1308. The magnitude of the horizontal dynamic component of acceleration may also be checked at 1306. Specifically, at 1306, a check is made whether the horizontal dynamic component of acceleration is less than 0.1 g. This would indicate a flight take off, landing or take off or a banking turn maneuver. In such instances, delivery of a medicament bolus is prohibited at 1308. If the conditions of 1302, 1304 and 1306 are met, delivery of the medicament bolus is permitted at 1310.

Figure 14:
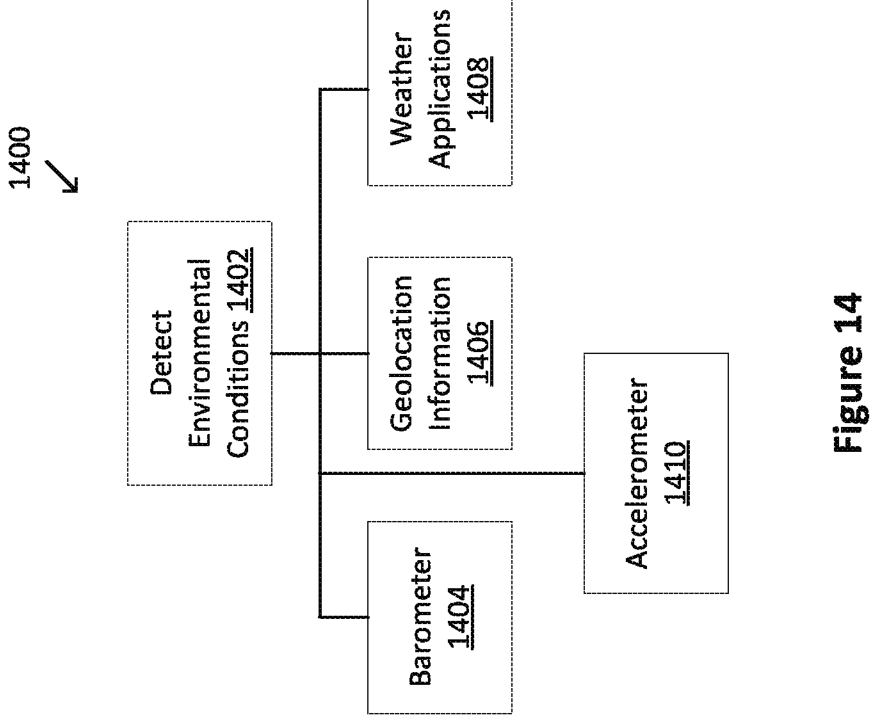
FIG. 14 depicts a diagram of various sources of data regarding environmental conditions that may be used in exemplary embodiments.

As was mentioned above, environmental conditions may be detected by gathering information from different sources. FIG. 14 depicts a diagram 1400 of illustrative sources for detecting environmental conditions 1402. The source may be a barometer 1404 as described above. The source may be a source of geolocation information 1406, like a GPS transceiver or a compass. The source may be a weather application 1408 resident on the management device 104 or on the medicament delivery device. Alternatively, the weather application 1408 may be a website that is accessible over the Internet or an intranet. The source also may be an accelerometer 1410 as detailed above. This depiction of sources of environmental data is intended to be illustrative and not limiting. Other sources may be used in some embodiments.

Figure 15A:
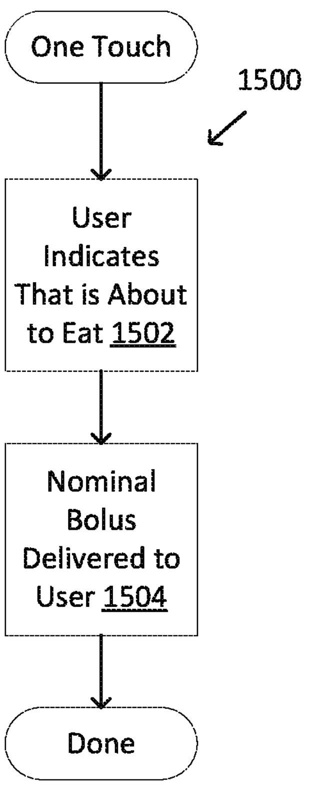
FIG. 15A depicts a flowchart of illustrative steps that may be performed in exemplary embodiments to provide one touch medicament bolus delivery.
Figure 15B:
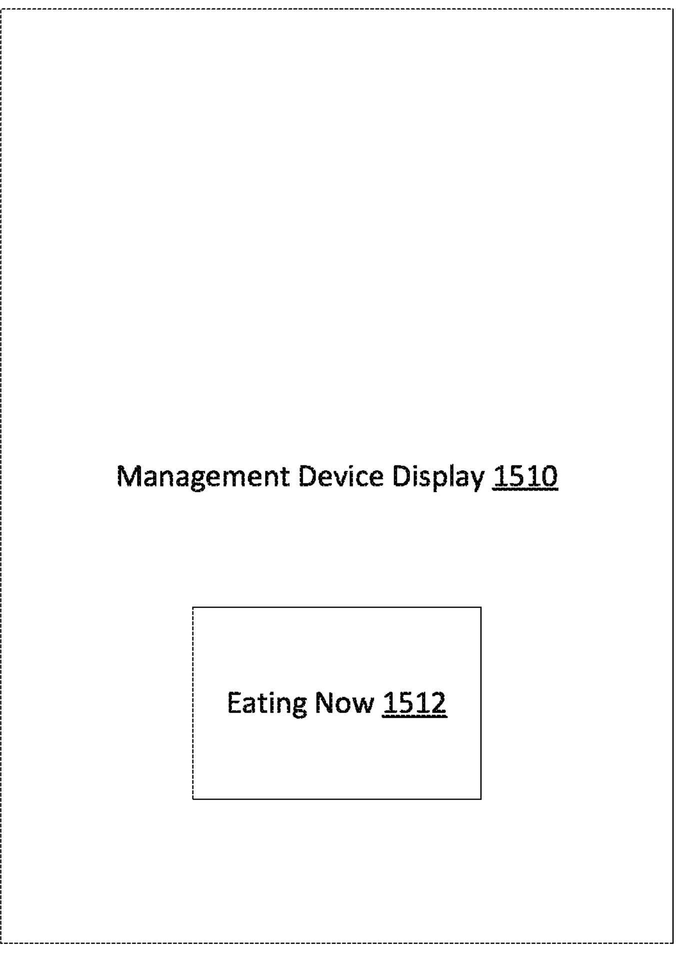
FIG. 15B depicts an illustrative user interface for one touch medicament bolus delivery in exemplary embodiments.

The changing environmental conditions, such as ambient air pressure, may make it difficult for the user 108 to determine the appropriate bolus size. The exemplary embodiments may solve this issue for the user 108 by calculating the medicament bolus dosage for the user 108 and simplifying how a user 108 requests a medicament bolus. FIG. 15A depicts a flowchart 1500 of illustrative steps that may be performed in exemplary embodiments to simplify the delivery a medicament bolus by the medicament delivery device 102. At 1502, the user 108 indicates that the user 108 is about to eat a meal and hence needs a medicament bolus. This example is for the case where the medicament is insulin or another medicament that reduces glucose levels for the user 108. The user 108 may indicate that the user 108 is about to eat by presenting a user interface like that shown in FIG. 15B. As shown, a selectable user interface element 1512, like a button or other user interface widget, is displayed on the display 1510 of the management device 104. The user 108 may select the user interface element 1512 to indicate that the user 108 is about to eat a meal and needs a meal bolus delivered.

Figure 16:
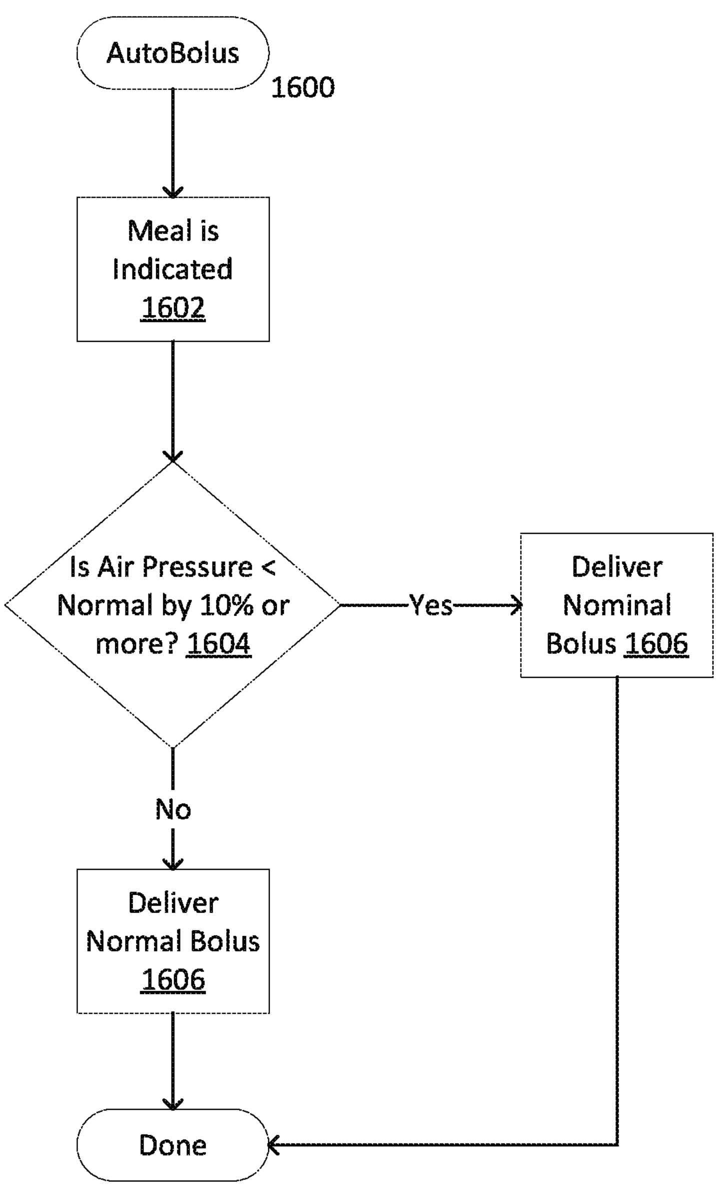
FIG. 16 depicts a flowchart of illustrative steps that may be performed in exemplary embodiments to determine a dosage for a medicament bolus based on ambient air pressure.

FIG. 16 depicts a flowchart of how the medicament delivery device decides what dosage of bolus to deliver based on environmental conditions. The process begins at 1602 with a meal be indicated, such as in response to selection of the user interface element 1512. A check is made whether the ambient air pressure is less than normal atmospheric air pressure by greater than 10% at 1604. If not, a normal bolus dosage is delivered at 1606. If so, at 1606 a nominal bolus of medicament is delivered by the medicament delivery device 102 to the user 108. The nominal bolus dosage is less than otherwise would be delivered to compensate for the reduced ambient air pressure. The nominal dosage may be determined using the following equation:

$$\text{Bolus Dosage}=0.08*TDI+(\text{current Glucose level}-150)/CF-\text{Insulin on Board}$$

where TDI is total daily insulin for the user 108 and CF is the correction factor for the user 108. The adjustment factor value of 0.8 adjusts the dosage to be a more conservative nominal value. The adjustment factor value may be modulated lower to a value, such as 0.7, if the ambient air pressure in more than 10% below normal atmospheric pressure.

Figure 17A:
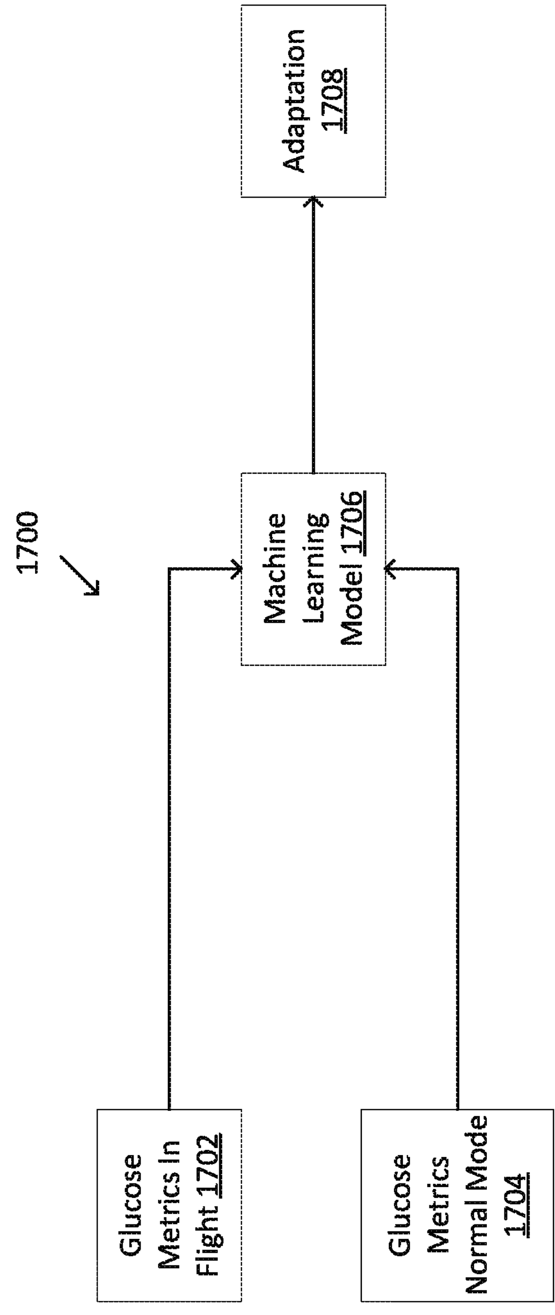
FIG. 17A depicts a diagram depicting an adaptation in settings resulting from processing of glucose metrics data by a machine learning model.

Machine learning may be applied in exemplary embodiments to improve the therapeutic outcomes of the user 108. Specifically, machine learning models may process data regarding the user 108 and the medicament deliveries to adjust the flight mode adaptation of settings. Consider the case where the medicament is insulin. FIG. 17A depicts a diagram 1700 illustrating the use of a machine learning model to make adaptations. As shown in the diagram 1700, glucose metrics while in flight mode 1702 and glucose metrics while in normal mode 1704 (collectively "glucose metrics") are input into a machine learning model 1706. The machine learning model 1706 may be, for example, a neural network, a random forest model, a support vector machine, fuzzy logic, a rules-based system or the like. The machine learning model 1706 processes and learns from the glucose metrics 1702 and 1704 to produce an adaptation 1708 to improve the therapeutic response realized by the medicament delivery device 102.

FIG. 17B depicts some of the glucose metrics 1710 that may be input into the machine learning model 1706 to produce the adaptation 1708. The glucose metrics 1710 include the time that the glucose of the user 108 was in the desired range 1712. The desired range may be between 70 to 180 mg/dL. The glucose metrics 1710 may also include the time that the glucose of the user 108 was above the desired range 1714 and the time that the glucose of the user was very much above the desired range 1716 (i.e., above 240 mg/dL). Similarly, the glucose metrics 1710 may include the time below the desired range 1718 and the time very below the desired range 1720 (i.e., below 60 mg/dL). The glucose metrics 1710 may further include the mean glucose value 1722 for the interval of interest over which the glucose values that are gathered. The glucose metrics 1710 may include the total insulin delivered for the interval of interest as normalized by number of meals or number of flight hours 1724. Still further, the glucose metrics 1710 may include the middle glucose value 1726 and the maximum glucose value 1728 for the interval of interest.

Figure 18A:
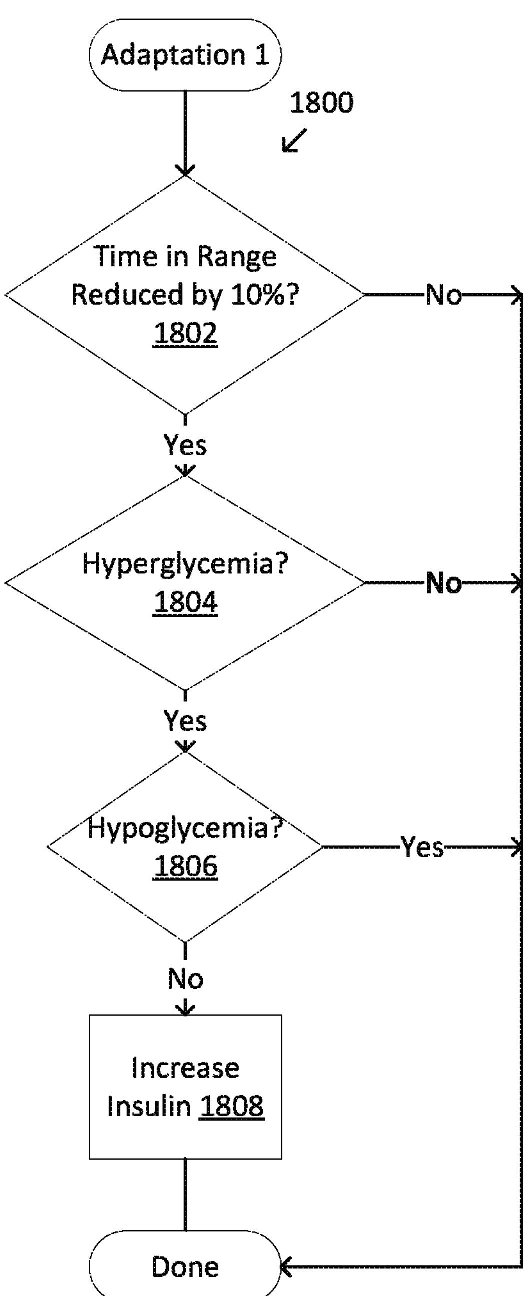
FIG. 18A depicts a flowchart of illustrative steps that may be performed in exemplary embodiments to make a first adaptation with the machine learning model.

Numerous adaptations may be made responsive to the glucose metrics. FIG. 18A depicts a flowchart 1800 of illustrative steps that may be performed in exemplary embodiments for one variety of adaptation. This adaptation checks at 1802 if the time in the desired range during flight mode is reduced by 10%. If not, no further action is taken. If so, a check is then made whether the user 108 has experienced hyperglycemia during the interval of concern at 1804. If not, no further action is taken. If so, at 1806, a check is made whether the user 108 has experienced hypoglycemia during the interval of interest at 1806. If the user has experienced hypoglycemia, no further action is taken. If the user has not experienced hypoglycemia, the insulin delivery is increased by the percentage such as five or 10% at 1808.

Figure 18B:
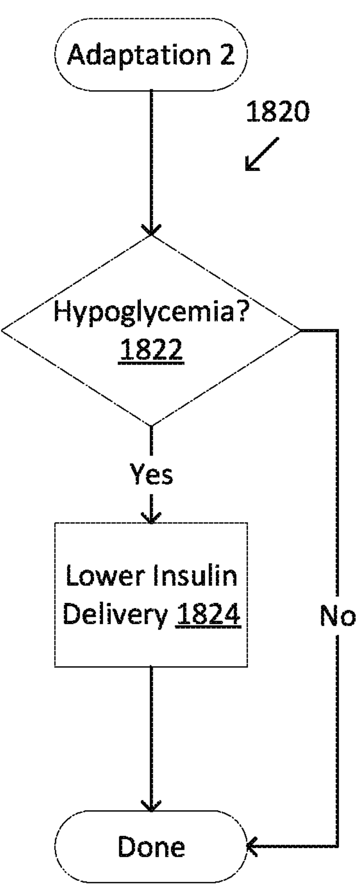
FIG. 18B depicts a flowchart of illustrative steps that may be performed in exemplary embodiments to make a second adaptation with the machine learning model.

FIG. 18B depicts a flowchart 1820 of illustrative steps that may be performed in exemplary embodiments to realize a second adaptation. At 1822, a check is made whether the user 108 has experienced hypoglycemia during the interval of interest. If not, no further action is taken. If so, the insulin delivery is lowered at 1824 by a fixed percentage such as by 5% or 10%.

The adaptations discussed relative to FIGS. 18A and 18B are intended to be merely illustrative examples of adaptations that may be performed by the machine learning model. Other adaptations may be realized in some embodiments.

While exemplary embodiments have been described herein, it should be appreciated that various changes in form and detail from the exemplary embodiments may be made without departing from the scope of the appended claims.

What is claimed is:

1. A method performed by a processor of an electronic device, comprising:

determining with the processor that a user of a medicament delivery device is on an airplane flight;

responsive to the determining with the processor, switching from a normal mode basal delivery rate of a medicament to the user by the medicament delivery device for when the user is not on the airplane flight to a flight mode basal delivery rate of the medicament to the user by the medicament delivery device, which is different from the normal mode basal delivery rate, when the user is on the airplane flight, to adapt for at least one environmental condition due to the user being on the airplane flight;

detecting that the airplane flight has landed; and responsive to the detecting that the airplane flight has landed, switching from the flight mode basal delivery rate of the medicament to the user by the medicament delivery device to a cool off mode basal delivery rate of the medicament to the user by the medicament delivery device, which is different from the normal mode basal delivery rate and the flight mode basal delivery rate, for a cool off period to aid in transition back to the normal mode basal delivery rate of the medicament to the user.

2. The method of claim 1, wherein the at least one environmental condition includes a reduced air pressure, and a bolus dosage of the medicament delivered by the medicament delivery device while operating at the flight mode basal delivery rate is less than a bolus dosage of the medication delivered by the medicament delivery device while operating at the normal mode basal delivery rate, responsive to the reduced air pressure.

3. The method of claim 1, wherein the at least one environmental condition includes a reduced air pressure and wherein the flight mode basal delivery rate is less than the normal mode basal delivery rate responsive to the reduced air pressure.

4. The method of claim 3, wherein the rate of delivery is reduced to suspend delivery of the medicament to the user by the medicament delivery device.

5. The method of claim 1, wherein the medicament is insulin.

6. The method of claim 1, wherein the method further comprises displaying a request for the user to confirm that the user is on the airplane flight and wherein the determining is based on receiving a response to the request where the response confirms that the user is on the airplane flight.

7. The method of claim 1, wherein the medicament delivery device also is configured to deliver boluses of medicament to the user.

8. The method of claim 1, wherein the determining is based on one or more of global positioning system (GPS) data, measurements by an accelerometer in the electronic device, an entry in an electronic calendar of the user, one or more pressure readings or network identification information for a network that is accessible to the electronic device.

9. A non-transitory storage medium storing computer programming instructions that when executed by a processor cause the processor to perform the following:

determine that a user of a medicament delivery device is on an airplane flight;

responsive to the determining that the user is on the airplane flight, switch from a normal mode basal delivery rate of a medicament to the user by the medicament delivery device for when the user is not on the airplane flight to a flight mode basal delivery rate of the medicament to the user by the medicament delivery device, which is different from the normal mode basal delivery rate, when the user is on the airplane flight to adapt for at least one environmental condition due to the user being on the airplane flight;

detect that the airplane flight has landed; and responsive to the detecting that the airplane flight has landed, switch from the flight mode basal delivery rate of the medicament to the user by the medicament delivery device to a cool off mode basal delivery rate of the medicament to the user by the medicament delivery device, which is different from the normal mode basal delivery rate and the flight mode basal delivery rate, for a cool off period to aid in transition back to the normal mode basal delivery rate of the medicament to the user.

10. The non-transitory storage medium of claim 9, wherein executing the computer programming instructions causes the processor to maintain the cool off mode for 1 to 7 days after the airplane flight has landed.

11. The non-transitory storage medium of claim 9, wherein the cool off mode basal delivery rate during the cool off period is an average basal delivery rate during the airplane flight.

12. The non-transitory storage medium of claim 9, wherein the at least one environmental condition includes a reduced air pressure, and a bolus dosage of the medicament delivered by the medicament delivery device while operating at the flight mode basal delivery rate is less than a bolus dosage of the medication delivered by the medicament delivery device while operating at the normal mode basal deliver rate, responsive to the reduced air pressure.

13. The non-transitory storage medium of claim 9, wherein the determining is based on one or more of global positioning system (GPS) data, measurements by an accelerometer in an electronic device comprising the non-transitory storage medium and the processor, an entry in an electronic calendar of the user, one or more pressure readings or network identification information for a network that is accessible to the electronic device.

14. The non-transitory storage medium of claim 9, wherein the computer programming instructions further contain instructions, that when executed by the processor, cause the processor to:

determine whether the airplane flight has traversed multiple time zones; and perform the switching to the cool off mode basal delivery rate only if it is determined that the airplane flight traversed multiple time zones.

15. A medicament delivery system, comprising:

a non-transitory storage medium storing computer programming instructions;

a processor configured to execute the computer programming instructions to cause the processor to:

determine that a user of a medicament delivery device is on an airplane flight;

responsive to the determining that the user is on the airplane flight, switch from a normal mode basal delivery rate of the medicament to the user by the medicament delivery device for when the user is not on the airline flight to a flight mode basal delivery rate of the medicament to the user by the medicament delivery device, which is different from the normal mode basal delivery rate of the medicament, when the user is on the airplane flight to adapt for at least one environmental condition due to the user being on the airplane flight;

detect that the airplane flight has landed; and responsive to the detecting that the airplane flight has landed, switch from the flight mode basal delivery rate of the medicament to the user by the medicament delivery device to a cool off mode basal delivery rate of the medicament to the user by the medicament delivery device, which is different from the normal mode basal delivery rate and the flight mode basal delivery rate, for a cool off period to aid in transition to the normal mode basal delivery rate of the medicament to the user.

16. The medicament delivery system of claim 15, wherein the cool off mode basal delivery rate is maintained for the cool off period of 1 to 7 days after the airplane flight has landed.

17. The medicament delivery system of claim 15, wherein the cool off mode basal delivery rate during the cool off period is an average basal delivery rate during the airplane flight.

18. The medicament delivery system of claim 15, wherein the at least one environmental condition includes a reduced air pressure, and wherein a bolus dosage of the medicament delivered by the medicament delivery device while operating at the flight mode basal delivery rate is less than a bolus dosage of the medication delivered by the medicament delivery device while operating at the normal mode basal deliver rate, responsive to the reduced air pressure.

19. The medicament delivery system of claim 15, wherein the determining is based on one or more of global positioning system (GPS) data, measurements by an accelerometer in an electronic device of the medicament delivery system, an entry in an electronic calendar of the user, one or more pressure readings or network identification information for a network that is accessible to the electronic device.

20. The medicament delivery system of claim 15, wherein executing the computer programming instructions further causes the processor to:

determine whether the airplane flight has traversed multiple time zones; and perform the switching to the cool off mode basal delivery rate only if it is determined that the airplane flight traversed multiple time zones.

* * * * *